(12) United States Patent
Campbell (10) Patent No.: US 7,531,715 B1
(45) Date of Patent: May 12, 2009

(54) DOUBLE NUCLEAR TRANSFER METHOD AND RESULTS THEREOF

(75) Inventor: Keith H. S. Campbell, Leicestershire (GB)

(73) Assignee: PPL Therapeutics (Scotland), Edinburgh (GB)

( * ) Notice: Subject to any disclaimer, the term of this patent is extended or adjusted under 35 U.S.C. 154(b) by 0 days.

(21) Appl. No.: 09/600,130

(22) PCT Filed: Jan. 13, 2000

(86) PCT No.: PCT/GB00/00086

§ 371 (c)(1),
(2), (4) Date: May 14, 2001

(87) PCT Pub. No.: WO00/42174

PCT Pub. Date: Jul. 20, 2000

(30) Foreign Application Priority Data

Jan. 13, 1999 (GB) ................................. 9900734.6

(51) Int. Cl.
C12N 15/00 (2006.01)
C12N 5/00 (2006.01)
C12N 5/02 (2006.01)
G01N 33/00 (2006.01)
A01K 67/027 (2006.01)

(52) U.S. Cl. .............................. 800/24; 800/3; 800/14; 800/21; 435/325

(58) Field of Classification Search ..................... 800/3, 800/21
See application file for complete search history.

(56) References Cited

U.S. PATENT DOCUMENTS

| 5,487,992 | A |   | 1/1996 | Capecchi et al. ......... 435/172.3 |
| 5,942,435 | A | * | 8/1999 | Wheeler ..................... 435/325 |
| 5,945,577 | A |   | 8/1999 | Stice et al. .................... 800/24 |
| 6,011,197 | A |   | 1/2000 | Strelchenko et al. |
| 6,525,243 | B1 | * | 2/2003 | Stockman Campbell et al. ........................... 800/24 |

FOREIGN PATENT DOCUMENTS

| EP | 0 633 314 A1 | 1/1995 |
| WO | WO 91/01140 | 2/1991 |
| WO | WO 94/24274 | 10/1994 |
| WO | WO 94/24301 | 10/1994 |
| WO | WO 95/20042 | 7/1995 |

OTHER PUBLICATIONS

Simerly, C et al., Molecular correlates of primate nuclear transfer failures, Science, 300:297, 2003.*
Vogel, G, 2003, Misguided chromosomes foil primate cloning, Science, 300:225 and 227.*
Kennedy, D. 2006, Editorial Retraction, Science, 311:335.*
Baguisi et al "Production of goats by somatic cell nuclear transfer" Nature Biotechnology (1999) 17: pp. 456-461.
R.O. Bates and B.N. Day "*The Attainment of Estrus in Sows Administered with 400 IU Pregnant Mare Serum Gonadotropin and 200 IU Human Chorionic Gonadotropin at Weaning[1]*" American Society of Animal Science Annual Meeting, New Brunswick, NJ, Jul. 19-22 (1989).
Betthauser et al. "*Production of cloned pigs from in vitro systems*" Nature Biotechnology. 18:1055-1059 (2000).
Booth et al, "*Application of the Zona-Free Manipulation Technique to Porcine Somatic Nuclear Transfer*", Cloning and Stem Cells vol. 3, No. 4, 2001 (Mary Ann Liebert, Inc.).
E.W. Carney and R.H. Foote "*Effects of superovulation, embryo recovery, culture system and embryo transfer on development of rabbit embryos in vivo and in vitro,*" J. Reprod. Fert. (1990) 89, 543-551.
Chen et al. "*Interspecies Implantation and Mitichondria Fate of Panda-Rabbit Cloned Embryos[1]*," Biology of Reproduction 67, 637-642 (2002).
Chesne et al. "*Cloned Rabbits produced by nuclear transfer from adult somatic cells*" Nature Biotechnology 20:366-369 (2002).
Choi et al. *Production of Nuclear Transfer Horse Embryos by Piezo-Driven Injection of Somatic Cell Nuclei and Activation with Stallion Sperm Cytosolic Extract[1]*, Biology of Reproduction 67, 561-567 (2002).
Chrenek, et al, "*Effects of Superovulationm Culture and Microninjection on Development of Rabbit Embryos in vitro,* "Theriogenology 50: 659-666 (1998).
Daniels, et al., "*Comparison of Gene Transcription in Cloned Bovine Embryos Produced by Different Nuclear Transfer Techniques*," Molecular Reproduction and Development 60:281-288 (2001).
Galli et al., "*Comparison of Microinjection (Piezo-Electric) and Cell Fusion for Nuclear Transfer Success with Different Cell Types in Cattle*," Cloning and Stem Cells vol. 4, pp. 189-196. No. 3, 2002.
Galli et al, "*Embryo Production By Ovum Pick Up From Live Donors*," Theriogenology 55:1341-1357 (2001).
Garcia-Ximinez et al., "*Embryo Transfer in Lactating Rabbit does by Laparoscopy*," Amm Reprod Soci 24. 343-346 (1991).

(Continued)

*Primary Examiner*—Valarie Bertoglio
(74) *Attorney, Agent, or Firm*—King & Spalding (57) ABSTRACT

A method is described for the production of an animal (offspring) by the process of nuclear transfer. The animal may be produced using donor genetic material in cells taken directly from any stage of an animal, such as an embryo, foetus or adult or from cell cultures established from material from any stage of an animal, such as embryonic, foetal or adult material. The process may be used to introduce genetic modifications into the resultant offspring by genetic manipulation and selection of the cells to act as nuclear donors prior to embryo reconstruction.

The present invention provides a method of reconstituting an animal embryo, the process comprising transferring a nucleus into a first oocyte followed by removing and transferring the nucleus from the oocyte to a further oocyte or to an enucleated fertilized zygote.

35 Claims, 1 Drawing Sheet

OTHER PUBLICATIONS

Gjorret et al., "*Ultrastructure of Oocyte Maturation, Fertilization, and Early Embryo Development In Vitro in the Siberian Tiger (Panthera Tigris Altaica)*" Molecular Reproduction and Development 63:79-88 (2002).

H.H. Herrmann, W. Holtz "*Culture of Pig Embryos Collected in Situ or After Slaughter*" Animal Reproduction Science, 4(1981) 143-147.

Hiroyoshi Hoshi "*In Vitro Production of Bovine Embryos and their Application for Embryo Transfer*" Theriogenology 59 (2003) 675-685.

Jin et al., "*Successful Pregnancy After Transfer of Rabbit Blastocysts Grown In Vitro From Single-Cell Zygotes*" Theriogenology 54:1109-1116 (2000).

Knott et al., Porcine Sperm Factor Supports Activation and Development of Bovine Nuclear Transfer Embryos[1] Biology of Reproduction 66 1095-1103 (2002).

Kubota et al., "*Six cloned Calves Produced from Adult Fibroblast Cells After Long-term Culture*" PNAS vol. 97 No. 3: pp. 990-995 (2000).

Lee et al., "*Cloned Zebrafish by Nuclear Transfer from Long-term-cultured Cells*" Nature biotechnology vol. 20:pp. 795-799 (Aug. 2002).

Li et al., "*Conditions for In Vitro Maturation and Artificial Activation of Ferret Oocytes*" Biology of Reproduction 66, 1380-1386 (2002).

Li et al., *Technical Note: Porcine Non-Surgical Embryo Transfer*[1] J Animal Science 74:2263-3368 (1996).

Loi et al. "*Genetic Rescue of an endangered mammal by cross-species nuclear transfer using post-mortem somatic cells*" Nature Biotechnologyvol. 19: pp. 962-964 (2001).

Love & Grey"*Early Abortion of Gilts as A Way Of Synchronising Oestrus and Improving Litter Size*"(1993).

Paul A. Martin, D.V.M., Ph.D. "*Embryo Transfer in Swine*" Embryo Transfer and Genetic Engineering 66-69.

Ogura et al., *Production of Male Cloned Mice from Fresh, Cultured, and Cryopreserved Immature Sertoli Cells* Biology of Reproduction 62:1579-1584 (2000).

Piotrowska et al., *Effects of Preactivation of Ooplasts or Synchronization of Blastomere Nucle in G1 on Preimplantation Development of Rabbit Serial Nuclear Transfer Embryos*[1] Biology of Reproduction 63, 677-682 (2000).

C.E. Pope *Embryo Technology in Conservation Efforts For Endangered Felids* Theriogenology 53:163-174 (2000).

Saikhun et al., "*Xenonuclear Transplantation of Buffalo (Bubalas bubalis) fetal and Adult Somatic Cell Nuclei Into Bovine (Bos Indicus) Oocyte Cytoplasm and their Subsequent Development*" Theriogenology 57:1829-1837 (2002).

Shin et al. "*A Cat Cloned by Nuclear Transplantation*" Nature vol. 415 p. 859 (Feb. 21, 2002).

Michelle Sims and N.L. First "*Production of Calves by Transfer of Nuclei From Cultured Inner Cell Mass Cells*" Proc. Natl. Acad. Sci. USA vol. 90:pp. 6143-6147 (Jun. 1993).

Techakumphu et al., "*Survival of Rabbit Embryos after Synchronous or Asynchronous Transfer*" Animal Reproduction Science 12:297-304 (1987).

Wakayama et al., "*Mice Cloned from Embryonic Stem Cells*" PNAS vol. 96:pp. 14984-14989 (Dec. 21, 1999).

Wilmut et al., "*Somatic Cell Nuclear Transfer*" Nature vol. 419:pp. 583-585 (Oct. 10, 2002).

Wood et al., "*Efficacy of Altrengost in Synchronizing Estrus in Two Swine Breeding Programs and Effects on Subsequent Reproductive Performance of Sows*[1]" J Anim, Sci. 70:1357-1364 (1992).

Woods et al., "*A Mule Cloned from Fetal Cells by Nuclear Transfer*" Sciencexpress p. 1-2 (May 29, 2003).

Arbonés, M.L., et al., "Gene targeting in normal somatic cells: inactivation of the interferon-γ receptor in myoblasts," *Nat. Genet.* 6:90-97, Macmillan Magazines Ltd (1994).

Bertling, W.M. et al., "Use of Liposomes, Viral Capsids, and Nanoparticles as DNA Carriers," *Biotechnol. Appl. Biochem.* 13:390-405, Academic Press, Inc. (1991).

Brandon, E.P., et al., "Targeting the mouse genome: a compendium of knockouts (part I)," *Curr. Biol.* 5:625-634, Current Biology Ltd. (1995).

Brandon, E.P., et al., "Targeting the mouse genome: a compendium of knockouts (part II)," *Curr. Biol.* 5:758-765, Current Biology Ltd. (1995).

Brandon, E.P., et al., "Targeting the mouse genome: a compendium of knockouts (part III)," *Curr. Biol.* 5:873-881, Current Biology Ltd. (1995).

Campbell, K.H.S., et al., "Sheep cloned by nuclear transfer from a cultured cell line," *Nature* 380:64-66, Macmillan Magazines Ltd. (1996).

Cao, X., et al., "Effects of fibroblast-mediated interleukin 3 and interleukin 6 gene therapy on hematopoiesis in mice treated with 5-fluorouracil," *J. Mol. Med.* 76:782-789, Springer-Verlag (Oct. 1998).

Cibelli, J.B., et al., "Transgenic bovine chimeric offspring produced from somatic cell-derived stem-like cells," *Nature Biotechnol.* 16:642-646, Macmillan Magazines Ltd. (Jul. 1998).

Cibelli, J.B., et al., "Production of Germline Chimeric Bovine Fetuses From Transgenic Embryonic Stem Cells," *Theriogenology* 47:241, Elsevier Science (Jan. 1997).

Cibelli, J.B., et al., "Cloned Transgenic Calves Produced from Nonquiescent Fetal Fibroblasts," *Science* 280:1256-1258, American Association for the Advancement of Science (May 1998).

Cole-Strauss, A., et al., "Correction of the Mutation Responsible for Sickle Cell Anemia by an RNA-DNA Oligonucleotide," *Science* 273:1386-1389, American Association for the Advancement of Science (1996).

Colman, A. and Garner, I., "Transgenic Animals in Science and Industry," *Pharm. Forum 5* (1996).

Deng, C. and Capecchi, M.R.,"Reexamination of Gene Targeting Frequency as a Function of the Extent of Homology between the Targeting Vector and the Target Locus," *Mol. Cell. Biol.* 12:3365-3371, American Society for Microbiology (1992).

Dominko, T., et al., "Bovine Docyte as a Universal Recipient Cytoplasm in Mammalian Nuclear Transfer," *Theriogenology* 49:385, Elsevier Science (Jan. 1998).

Fiering, S., et al., "An 'in-out' using gene targeting and FLP recombinase for the functional dissection of complex DNA regulatory elements: Analysis of the β-globin locus control region," *Proc. Natl. Acad. Sci. USA* 90:8469-8473, National Academy of Sciences (1993).

Finn, G.K., et al., "Homologous Plasmid Recombination Is Elevated in Immortally Transformed Cells," *Mol. Cell. Biol.* 9:4009-4017, American Society for Microbiology (1989).

Fulka, J., et al., "Cloning by somatic cell nuclear transfer," *Bioessays* 20:847-851, John Wiley and Sons, Inc. (Oct. 1998).

Hanson, K.D. and Sedivy, J.M., "Analysis of Biological Selections for High-Efficiency Gene Targeting," *Mol. Cell. Biol.* 15:45-51, American Society for Microbiology (1995).

Hortelano, G., et al., "Persistent Delivery of Factor IX in Mice: Gene Therapy for Hemophilila Using Implantable Microcapsules," *Human Gene Ther.* 10:1281-1288, Mary Ann Liebert, Inc. (May 1999).

Itzhaki, J.E., et al., "Construction by gene targeting in human cells of a 'conditional' CDC2 mutant that rereplicates its DNA," *Nature Genetics* 15:258-265, Macmillan Magazines, Ltd. (1997).

Johnson, R.S., et al., "Targeting of Nonexpressed Genes in Embryonic Stem Cells Via Homologous Recombination," *Science* 245:1234-1236, American Association for the Advancement of Science (1989).

Kato, Y. and Tsunoda, Y., "Totipotency and Pluripotency of Embryonic Nuclei in the Mouse," *Mol. Reprod. Develop.* 36:276-278, Wiley-Liss, Inc. (1993).

Kato, Y., et al., "Eight Calves Cloned from Somatic Cells of a Single Adult," *Science* 282:2095-2098, American Association for the Advancement of Science (Dec. 1998).

Kono, T., "Nuclear transfer and reprogramming," *Reviews Reprod.* 2:74-80, Society for the Study of Fertility (1997).

Kren, B.T., et al., "In Vivo site-directed mutagenesis of the *factor IX* gene by chimeric RNA/DNA Oligonucleotides," *Nature Med.* 4:285-290, Macmillan Magazines Ltd. (Mar. 1998).

Kubota, C., et al., "Six cloned calves produced from adult fibroblast cells after long-term culture," *Proc. Natl. Acad. Sci. USA* 97:990-995, National Academy of Sciences (Feb. 2000).

Kwon, O.Y. and Kono, T., "Production of identical sextuplet mice by transferring metaphase nuclei from four-cell embryos," *Proc. Natl. Acad. Sci. USA* 93:13010-13013, National Academy of Sciences (1996).

Liang, F., et al., "Chromosomal double-strand break repair in Ku80-deficient cells," *Proc. Natl. Acad. Sci. USA* 93:8929-8933, National Academy of Sciences (1996).

Lukacsovich, T., et al., "Repair of a specific double-strand break generated within a mammalian chromosome by yeast endonuclease I-*SceI*," *Nucl. Acids Res.* 22:5649-5657, Oxford University Press (1994).

Ma, T., et al., "Generation and Phenotype of a Transgenic Knockout Mouse Lacking the Mercurial-Insensitive Water Channel in Aquaporin-4," *J. Clin. Invest.* 100:957-962, Rockefeller University Press, Inc. (1997).

McCreath, K.J., et al., "Production of gene-targeted sheep by nuclear transfer from cultured somatic cells," *Nature* 405:1066-1069, Macmillan Magazines Ltd. (Jul. 2000).

McWhir, J., et al., "Selective ablation of differentiated cells permits isolation of embryonic stem cell lines from murine embryos with a non-permissive genetic background," *Nat. Genet.* 14:223-226, Macmillan Magazines Ltd. (1996).

Mitalipova, M., et al., "Bovine Oocyte Cytoplasm Reprograms Somatic Cell Nuclei from Various Mammalian Species," *Theriogenology* 49:389, Elsevier Science (Jan. 1998).

Müller-Ladner, U., et al., "Gene Transfer of Cytokine Inhibitors into Human Synovial Fibroblasts in the SCID Mouse Model," *Arthritis & Rheum.* 42:490-497, John Wiley and Sons, Inc. (Mar. 1999).

Nickoloff, J.A. and Reynolds, R. J., "Transcription Stimulates Homologous Recombination in Mammalian Cells," *Mol. Cell. Biol.* 10:4837-4845, American Society for Microbiology (1990).

Piedrahita, J. A., et al., "Generation of Transgenic Porcine Chimeras Using Primordial Germ Cell-Derived Colonies," *Biol. Reprod.* 58:1321-1329, Society for the Study of Reproduction (May 1998).

Porter, A.C.G. and Dallman, M.J., "Gene Targetting. Techniques and Applications to Transplantation," *Transplantation* 64:1227-1235, Williams and Wilkins (1997).

Prather, R.S., et al., "Nuclear Transplantation in Early Pig Embryos," *Biol. Reprod.* 41:414-418, Society for the Study of Reproduction (1989).

Prather, R.S. and First, N.L., "Cloning embryos by nuclear transfer," *J. Reprod. Fert. 41 suppl.*:125-134, Society for the Study of Fertility (1990).

Ramírez-Solis, R. and Bradley, A., "Advances in the use of embryonic stem cell technology," *Curr. Opin. Biol. Biotechnol.* 5:528-533, Current Biology Ltd. (1994).

Régulier, E., et al., "Continuous delivery of human and mouse erythropoietin in mice by genetically engineered polymer encapsulated myoblasts," *Gene Ther.* 5:1014-1022, Stockton Press (Aug. 1998).

Ross, M.E., et al., "Identification of a Functional Glucocorticoid Response Element in the Phenylethanolamine N-Methyltransferase Promoter Using Fusion Genes Introduced into Chromatin Cells in Primary Culture," *J. Neurosci.* 10:520-530, Society for Neuroscience (1990).

Russell, D.W. and Hirata, R.K., "Human gene targeting by viral vectors," *Nat. Genet.* 18:325-330, Macmillan Magazines Ltd. (Apr. 1998).

Sargent, R.G., et al., "Repair of Site-Specific Double-Strand Breaks in a Mammalian Chromosome by Homologous and Illegitimate Recombination," *Mol. Cell. Biol.* 17:267-277, American Society for Microbiology (1997).

Scheerer, J.B. and Adair, G.M., "Homology Dependence of Targeted Recombination at the Chinese Hamster *APRT* Locus," *Mol. Cell. Biol.* 14:6663-6673, American Society for Microbiology (1994).

Schnieke, A.E., et al., "Human Factor IX Transgenic Sheep Produced by Transfer of Nuclei from Transfected Fetal Fibroblasts," *Science* 278:2130-2133, American Association for the Advancement of Science (1997).

Sedivy, J.M. and Dutriaux, A., Gene targeting and somatic cell genetics: a rebirth or a coming of age?: *Trends Genet.* 15:88-90, Elsevier Science (Mar. 1999).

Shesely, E.G., et al., "Correction of a human $\beta^5$-globin gene by gene targeting," *Proc. Natl. Acad. Sci. USA* 88:4294-4298, National Academy of Sciences (1991).

Shim, H., et al., "Isolation of Pluripotent Stem Cells from Cultured Porcine Primordial Germ Cells," *Biol. Reprod.* 57:1089-1095, Society for the Study of Reproduction (1997).

Smith, A., "Cell therapy: In search of pluripotency," *Curr. Biol.* 8:R802-R804, Current Biology Ltd. (Nov. 1998).

Smithies, O., et al., "Insertion of DNA sequences into the human chromosomal β-globin locus by homologous recombination," *Nature* 317:230-234, Macmillan Magazines Ltd. (1985).

Stacey, A., et al., "Use of Double-Replacement Gene Targeting to Replace the Murine α-lactalbumin Gene with Its Human Counterpart in Embryonic Stem Cells and Mice," *Mol. Cell. Biol.* 14:1009-1016, American Society for Microbiology (1994).

Stacey, A., et al., "Lactation is disrupted by α-lactalbumin deficiency and can be restored by human α-lactalbumin gene replacement in mice," *Proc. Natl. Acad. Sci. USA* 92:2835-2839, National Academy of Sciences (1995).

Stewart, C.L., et al., "Stem Cells from Primordial Germ Cells Can Reenter the Germ Line," *Dev. Biol.* 161:626-628, Academic Press, Inc. (1994).

Stice, S.L., et al., "Cloning: New Breakthroughs Leading to Commercial Opportunities," *Theriogenology* 49:129-138, Elsevier Science (Jan. 1998).

Stinnakre, M.G., et al., "Creation and phenotypic analysis of α-lactalbumin-deficient mice," *Proc. Natl. Acad. Sci. USA* 91:6544-6548, National Academy of Sciences (1994).

Strauss, M., "The site-specific correction of genetic defects," *Nature Med.* 4:274-275, Macmillan Magazines Ltd. (Mar. 1998).

Suraokar, M. and Bradley, A., "New and Views. Targeting Sheep," *Nature* 405:1004-1005, Macmillan Magazines Ltd. (Jun. 2000).

Te Riele, H., et al., "Highly efficient gene targeting in embryonic stem cells through homologous recombination with isogenic DNA constructs," *Proc. Natl. Acad. Sci. USA* 89:5128-5132, National Academy of Sciences (1992).

Thyagarajan, B., et al., "The effect of target site transcription on gene targeting in human cells in vitro," *Nucl. Acids Res.* 23:2784-2790, Oxford University Press (1995).

Thyagarajan, B., et al., "Characterization of homologous DNA recombination activity in normal and immortal mammalian cells," *Nucl. Acids Res.* 24:4084-4091, Oxford University Press (1996).

Trounson, A. and Pera, M., "Potential benefits of cell cloning for human medicine," *Reprod. Fertil. Dev.* 10:121-125, CSIRO Publishing (Jan. 1998).

Vignon, X., et al., "Development of Bovine Nuclear Transfer Embryos Reconstituted with Quiescent and Proliferative Skin Fibroblasts," *Theriogenology* 51:216, Elsevier Science (Jan. 1999).

Wakayama, T., et al., "Full-term development of mice from enucleated oocytes injected with cumulus cell nuclei," *Nature* 394:369-374, Macmillan Magazines Ltd. (Jul. 1998).

Wells, D.N., et al., "The Use of Adult Somatic Cell Nuclear Transfer to Preserve the Last Surviving Cow of the Enderby Island Cattle Breed," *Theriogenology* 51:217, Elsevier Science (Jan. 1999).

Wheeler, M.B., "Development and Validation of Swine Embryonic Stem Cells: a Review," *Reprod. Fertil. Dev.* 6:563-568, CSIRO Publishing (1994).

Wilmut, I. et al., "Viable offspring derived from fetal and adult mammalian cells," *Nature* 385:810-813 (1997).

Wolf, E., et al., "Nuclear transfer in mammals: Recent developments and future perspectives," *J. Biotech.* 65:99-110, Elsevier Science (Oct. 1998).

Wu, H., et al., "Double replacement: Strategy for efficient introduction of subtle mutations into the murine *Colla-1* gene by homologous recombination in embryonic stem cells," *Proc. Natl. Acad. Sci. USA* 91:2819-2823, National Academy of Sciences (1994).

Yáñez, R.J. and Porter, A.C.G., "Therapeutic gene targeting," *Gene Ther.* 5:149-159, Stockton Press (Feb. 1998).

Zakhartchenko, V., et al., "Nuclear Transfer in the Bovine Embryo: Developmental Potential of Cultured Adult Cells," *Theriogenology* 51:218, Elsevier Science (Jan. 1999).

Zhen, L., et al., "Gene targeting of X chromosome-linked chronic granulomatous disease locus in a human myeloid leukemia cell line and rescue by expression of recombinant gp91$^{phox}$," *Proc. Natl. Acad. Sci. USA* 90:9832-9836, National Academy of Sciences (1993).

Dialog File 351, Accession No. 11714391, Derwent WPI English language abstract for WO 98/06834 (Document AM3).

Pending U.S. Appl. No. 09/475,674, Colman et al., filed Dec. 30, 1998.

Pending U.S. Appl. No. 09/614,864, Colman et al., filed Jul. 12, 2000.

* cited by examiner

FIG. 1
OVERVIEW OF DOUBLE NUCLEAR TRANSFER METHODOLOGY

DOUBLE NUCLEAR TRANSFER METHOD AND RESULTS THEREOF

This is the U.S. National Stage Application of PCT/GB00/00086, the entire disclosure of which is incorporated herein by reference.

A method is described for the production of an animal (offspring) by the process of nuclear transfer. The animal may be produced using donor genetic material in cells taken directly from any stage of an animal, such as an embryo, foetus or adult or from cell cultures established from material from any stage of an animal, such as embryonic, foetal or adult material. The process may be used to introduce genetic modifications into the resultant offspring by genetic manipulation and selection of the cells to act as nuclear donors prior to embryo reconstruction. In addition, the process may be used to produce animals containing multiple genetic modifications by a number of routes including but not limited to; i) introduction of multiple genetic modifications concomitantly into the cultured cell population ii) repeated rounds of transfection and selection of the cultured cell population iii) repeated rounds of transfection, selection, nuclear transfer and re-isolation of a cell population from the embryo, foetus, juvenile or adult animal so formed iv) or any combination thereof. The process may be used to de-differentiate cells (including embryonic, foetal or adult somatic cells) for the production of undifferentiated cells, Embryonic Stem cells, other stem cell populations, germ cells or their derivatives or differentiated somatic cell populations preferably from embryonic foetal or adult stages of nuclear transfer reconstructed embryos.

The technique of nuclear transfer allows the production of offspring by the reconstruction of an animal embryo (which throughout this text includes all concepts of an animal embryo such as an oocyte, egg, zygote or an early embryo). Genetic material from a donor cell (karyoplast) is transferred to a suitable recipient cell from which the nuclear or genomic genetic material has been removed. In the first demonstrations of this technique successful development was only obtained when the donor genetic material was taken from undifferentiated cells or blastomeres from early embryos. Subsequently, development has been obtained using donor genetic material from differentiated cells maintained in culture and isolated from embryonic (Campbell et al. Nature (1996) 380:64-66), foetal and adult tissues (Wilmut et al Nature (1997) 385: 810-813) and in published applications WO 97/07669 and WO 97/07668, the content of which are incorporated by reference into the present application in full including all table and diagrams. Subsequently live offspring have been obtained in the mouse using quiescent cell populations derived directly ex vivo as nuclear donors (Wakayama et al., Nature (1998) 394:369-373). The successful use of differentiated cells has now been particularly demonstrated in sheep, cattle and mice.

The use of nuclear transfer (NT) technology has many benefits and uses in the production of mammalian embryos, foetuses and offspring. These include but are not limited to;

1. The ability to carry out precise genetic modification of cultured cells to be used as nuclear donors prior to embryo reconstruction. Such modifications include but are not limited to, random gene addition, addition of multiple copies of a transgene, addition of a transgene at a precise location (targeted addition or knockin), gene removal (knockout), gene inactivation by targeted insertion, gene replacement, modification of any gene or its control sequences and gene multiplication.
2. The ability to carry out multiple genetic modifications in a single animal either by multiple genetic modifications of a cell population in culture or by sequential genetic modification, nuclear transfer and re-isolation of a cell population from the embryo, foetus or animal so produced.
3. The ability to increase the lifespan of cultured cell populations to be used for genetic modification by nuclear transfer and re-isolation of a cell population from the embryo, foetus, juvenile or adult animal so produced.
4. The ability to produce multiple copies of an animal from a genetically modified selected and cloned cell population.
5. The ability to produce multiple copies of any embryo, foetus, juvenile or adult animal by nuclear transfer from cells taken directly ex vivo or cell populations derived from any tissues taken from any of these stages with or without culture in vitro.
6. The ability to produce true clones by utilising oocytes from the maternal line of the cell donor as cytoplast recipients for embryo reconstruction
7. The ability to store intact genomes for long periods (e.g. by freezing cell populations in liquid N2) and to subsequently use these stored cells for the production of offspring by nuclear transfer.
8. The ability to dedifferentiate somatic nuclei and to produce undifferentiated cells that may be used for production of chimeric embryos, foetuses and adult animals by embryo aggregation or injection or to produce embryonic stem or embryonic germ cell populations.
9. The ability to dedifferentiate any somatic cell type by nuclear transfer and to isolate from the embryo so produced embryonic stem cells, germ cells or any other desired specialised or unspecialised cell type e.g. neurones.

Genetic modification of animals and the production of stem cell and differentiated cell populations by nuclear transfer technology have numerous uses in the fields of human medicine, agriculture, genetic preservation and research. These include but are not limited to the production of human therapeutic proteins in bodily fluids, disease prevention, increasing required production traits, cell based therapies, cell based delivery systems for genetic therapy, tissue and organ transplantation. The uses of such technology have been previously discussed in many manuscripts and patents. Two of these are WO 98/30683 and WO 98/39416. The present invention is applicable to all stages of animals (cells, tissues, embryos and whole animals), in particular animals of an ungulate species including, a cow, bull, pig, goat, sheep, camel or water buffalo, as well as a mouse, rat or other rodent, and also lagomorph animals, such as a rabbit. The invention does not relate to human reproductive cloning. It does cover human tissue cells and where applicable, human embryos, in particular those embryos under 14 days old.

In general, oocytes arrested at metaphase of the second meiotic division have been used as cytoplast recipients. The donor genetic material has been introduced into the recipient cell cytoplasm by the processes of 1) cell fusion 2) injection of intact cells, lysed cells or nuclei. Transfer of genetic material may occur either at the time of activation, preceding activation (see patent applications WO 97/07669 and WO 97/07668 or following activation (Campbell et al., Biol. Reprod. 49 9330942 (1993); Campbell et al Biol. Reprod. 50 1385-1393 (1994)). In each of these instances the ploidy of the reconstructed embryo must be maintained by the use of donor genetic material at an appropriate stage of the cell cycle (for review see Campbell et al., Reviews of Reproduction 1:40-46 (1996)). This process may be coupled with genetic manipulation techniques for the production of transgenic offspring (Schnieke et al., Science 278:2130-2133 (1997)). The use of nuclear transfer coupled to genetic modification of cells in culture and their selection prior to animal production has a number of advantages including;

1. production of non-mosaic animals ensuring germ line transmission of the genetic modification/s
2. An increased efficiency in the production of such genetically modified animals.
3. The production of multiple copies of the offspring thereby reducing the generation interval to produce flocks or herds for production purposes or increasing the numbers of animals for dissemination of genetic modification into the population as a whole.
4. The production of animals containing multiple genetic modifications.
5. The production of transgenic animals with superior expression characteristics by utilisation of the pre-selection of the integration site of the transgene.

In pigs, the use of nuclear transfer for the production of live offspring has been associated with difficulties. Although offspring have been produced by swapping the pronuclei of fertilised zygotes, only 1 piglet has been produced from a later developmental stage (4 cell) (Prather et al., *Biol Reprod* 1989 September 41:3 414-8).

The process of embryo reconstruction and production of viable offspring by nuclear transfer is a multistep procedure. Each of these steps will now be described in more detail prior to a description of the present invention as a whole. The steps are those included in the present invention. The description below is intended to give explanation to the steps and is not an exhaustive nor limiting description.

THE RECIPIENT CELL OR CYTOPLAST

Oocytes, fertilised zygotes and two cell embryos have been used as cytoplast recipients for nuclear transfer. In general oocytes arrested at metaphase of the second meiotic division (also termed unfertilised eggs) have become the cytoplast of choice. At this point in oocyte development the genetic material is arranged upon the meiotic spindle and is easily removed using mechanical means. Several reports have demonstrated that during maturation i.e. between the germinal vesicle stage (prophase of the first meiotic division) and arrest at metaphase of the second meiotic division genomic DNA can be removed and the resulting cytoplast used for nuclear transfer (Kato Y., Tsunoda Y., *Mol Reprod Dev* (1993) October 36:2 276-8). The use of fertilised zygotes as cytoplast recipients has been reported in mouse (Kwon O. Y., Kono T., Proc Natl Acad Sci U.S.A (1996) November 12, 93:23 13010-3), cattle (Prather R. S., First N. L., J Reprod Fertil Suppl (1990) 41:), and pigs (Prather et al., *Biol Reprod* (1989) September 41:3, 414-8). In cattle and pigs, development of embryos reconstructed using zygotes as cytoplast recipients is low and on the whole restricted to the exchange of pronuclei, suggesting that factors essential for successful development are removed with the pronuclei. The subject matter of the present invention is to produce a pronucleus-like structure (including a pronucleus) by transfer of a suitable nucleus, preferably to an enucleated Metaphase II oocyte. The pronucleus-like structure thus formed will contain factors, which are generally removed during zygote enucleation. This pronucleus-like structure is then used as a donor of genetic material for a second nuclear transfer embryo reconstruction. Nuclei or cells of any cell cycle stage may be used as donors of genetic material preferably however; the cell cycle stage of the recipient cytoplast must be controlled accordingly.

Preparation of a Cytoplast Recipient by Removal of the Genomic Genetic Material.

This process has in general been termed enucleation. In the majority of recipients utilised, the genomic DNA is not enclosed within a nuclear membrane at the time of removal. The removal of the genetic material according to the present invention and described by the term "enucleation" does not require that the genetic material is present in a nuclear membrane (it may or may not be, or may partially be). Enucleation may be achieved physically by actual removal of the nucleus, pronuclei or metaphase plate (depending on the recipient cell), or functionally, such as by the application of ultra-violet radiation or another enucleating influence. Removal of the genetic material is possible by physical and/or chemical means. In the early reports of nuclear transfer, MII oocytes were simply cut in half on the basis that one half would contain the genetic material and the other would not. Modifications to this approach have been made in order to reduce the volume of cytoplasm, which was removed. This may be achieved by aspiration of a small amount of cytoplasm from directly beneath the first polar body using glass micropipettes or by using a knife to cut away that part of the oocyte beneath the polar body. To facilitate plasticity of the oocyte it may be pre-treated with the microtubule inhibitor Cytochalasin B or other such agent that disrupts the cytoskeleton. In contrast to physical enucleation, chemical treatment has been demonstrated to cause complete removal of the genetic material in the mouse.

Treatment of maturing oocytes with the Topoisomerase inhibitor ectoposide results in the expulsion of all genomic material with the first polar body (Elsheikh A. S. et al Jpn J Vet Res (1998) February 45:4, 217-20), however no development to term has been described using cytoplast recipients produced by this method and there are no reports of this procedure in other species. Centrifugation of MII oocytes combined with Cytochalasin B treatment has been reported to cause enucleation in hamster and cattle oocytes (Tatham et al., *Hum Reprod* (1996) July 11:7 1499-503). The development of embryos reconstructed from such cytoplasts has been reported in cattle however the frequency of development is low.

When using zygotes, the genetic material may be removed by mechanical aspiration of both pronuclei. Dependent upon species, in order to facilitate visualisation of the pronuclei the zygotes may be centrifuged prior to enucleation.

Introduction of Genetic Material (Embryo Reconstruction).

Having prepared a suitable recipient cell or cytoplast the donor genetic material must be introduced. Various techniques have been reported including;

1. Cell fusion induced by chemical, viral or electrical means.
2. Injection of an intact cell by any method
3. Injection of a lysed or damaged cell.
4. Injection of a nucleus.

Any of these methods may be used in any species with some modifications of individual protocols.

Activation of the Reconstructed Embryo.

In addition to the transfer of donor genetic material from the karyoplast to the cytoplast, the cytoplast must be stimulated to initiate development. When using a fertilised zygote as a cytoplast recipient development has already been initiated by sperm entry at fertilisation. When using MII oocytes as cytoplast recipients the oocyte must be activated by other stimuli. Various treatments have been reported to induce oocyte activation and promote early embryonic development including, but not limited to; application of a DC electric stimulus, treatment with ethanol, ionomycin, Inositol tris-phosphate ($IP_3$), calcium ionophore A23187, treatment with extracts of sperm or any other treatment which induces calcium entry into the oocyte or release of internal calcium stores and results in initiation of development. In addition any of these treatments, alone or in combination, their application at the same or different times or in combination with inhibitors of protein synthesis (i.e. cycloheximide or puromycin) or inhibitors of serine threonine protein kinases (i.e. 6-DMAP) may be applied.

Culture of Reconstructed Embryos.

Nuclear transfer reconstructed embryos may be cultured in vitro to a stage suitable for transfer to a final recipient using any suitable culture medium or culture process. Alternatively, embryos may be cultured in vivo in the ligated oviduct of a suitable host animal (in general sheep) until a stage suitable for transfer to a final surrogate recipient is reached. Embryos from cattle, sheep and other species may be cultured in a trans species recipient, for simplicity a sheep provides a suitable recipient for bovine, ovine and porcine species. In order to prevent mechanical damage or attack by macrophages to the reconstructed embryos whilst in the oviduct of the temporary recipient it is usual to embed the embryos in a protective layer of agar or similar material.

The in vitro culture systems presently available for porcine embryos support development to the blastocyst stage, however, the frequency of live births from such embryos is low (Machaty et al., *Biology of Reproduction*, (1998) 59, 451-455). In the present invention the first nuclear transfer reconstructed embryo may be cultured by any of these methods until the formation of a pronuclear-like body occurs and the embryo is used for the second nuclear transfer reconstruction. In practice it is presently preferred that this first culture period is carried out using a suitable medium in vitro.

Figure 1:
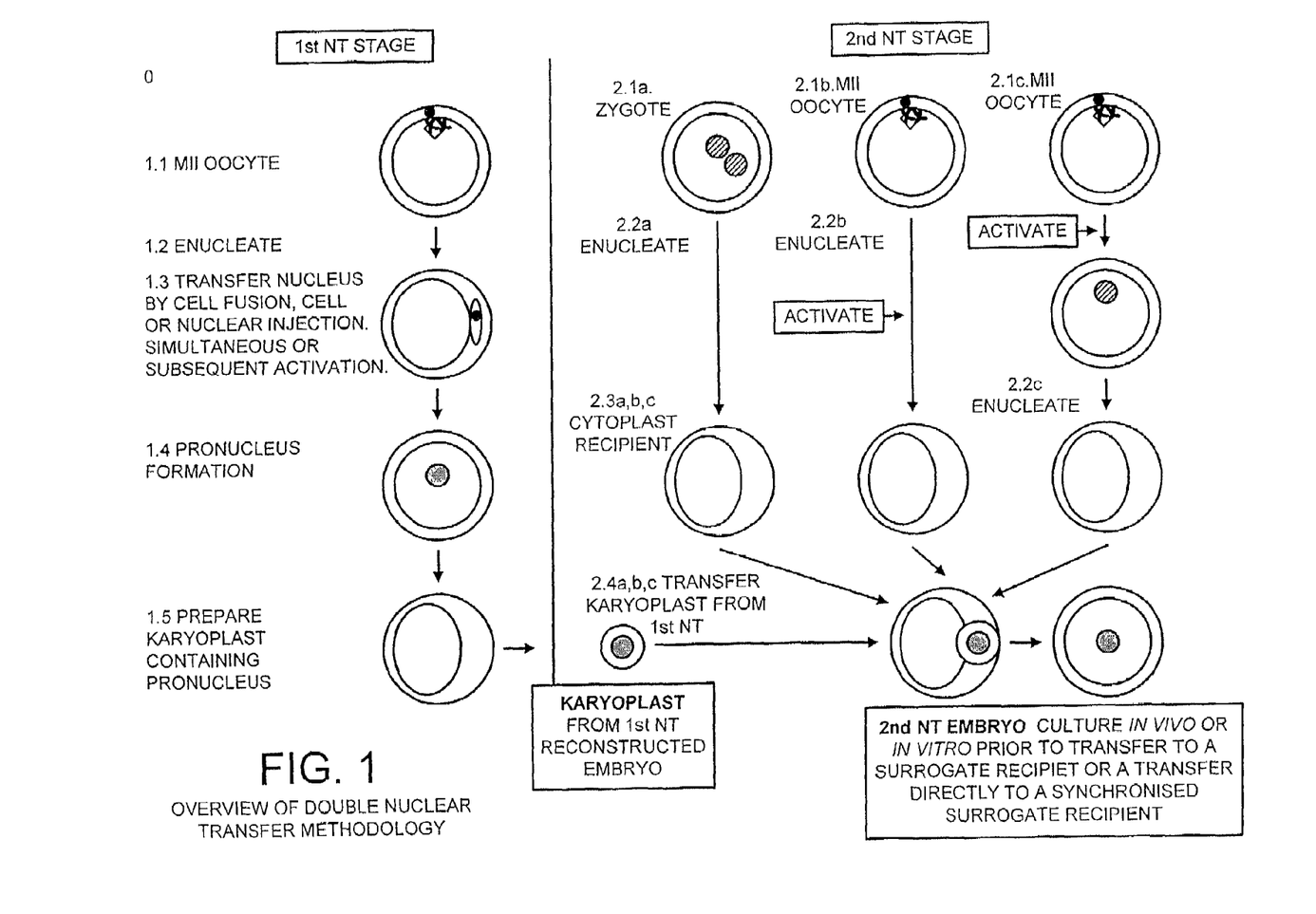
FIG. 1 is a schematic overview of double nuclear transfer methodology generally as described herein.

Each of the steps involved in the reconstruction of mammalian embryos by nuclear transfer is inefficient. In pigs this is particularly evident by the lack of reports on the production of live offspring from nuclear transfer reconstructed embryos. The basis of the present invention is to minimise the inefficient steps involved in the reconstruction process using a multistep embryo reconstruction procedure and culturing the embryos in the final surrogate recipient. Accordingly, one aspect of the invention provides a method of reconstituting an animal embryo. The process comprising transferring a nucleus into a first oocyte followed by removing and transferring said nucleus from said oocyte to a further recipient cell. Preferably, the nucleus transferred from the first oocyte is in the form of a pronucleus-like structure. Preferably, the second recipient cell is an oocyte or an enucleated fertilised zygote. This involves a double nuclear transfer procedure; The first step of this procedure is to produce a pronucleus-like structure by transfer of a donor nucleus to an oocyte. Preferably the oocyte is a mature metaphase II oocyte (unfertilised egg), which has been previously or is simultaneously or subsequently activated, or an activated MII oocyte (the activation is usually by physical or chemical input). An example of the first step is shown in FIG. 1 (for simplicities sake, the use of an activated recipient in FIG. 1 is not shown, but this is documented in Table 1). In the second step of the procedure the pronucleus-like structure generated by the first step is removed from the first reconstructed embryo and transferred to an oocyte or to an activated parthenote or enucleated fertilised zygote (FIG. 1). Where the transfer is to an oocyte, preferably the pronucleus-like structure is removed from the first reconstructed embryo and transferred to an oocyte which is an enucleated MII oocyte prior to, concomitant with or following activation. Following the second nuclear transfer the reconstructed embryo may be transferred directly to a final surrogate recipient for development to term.

The donor genetic material for embryo reconstruction can be provided by any differentiated, partially differentiated or undifferentiated cell taken directly from any stage in an animal development, such as an embryo, foetus, juvenile or adult animal or any cell line derived from such. In previous reports the cell cycle stage of the donor nucleus has been shown to be critical for development. In the present invention a cell at any stage of the cell cycle can be used as donor of genetic material for the first reconstruction process. However, the combination of cell cycle stages of the donor nucleus and the recipient cytoplasm will vary dependent upon the cell cycle stage of the cell to be used as donor of genetic material at the time of transfer. The donor genetic material and the recipient cells, are not required to be from the same animal species, although this may be preferred.

Preparation of Donor Cells.

Methods and materials for the culture, synchronisation and selection of donor cells to be used as nuclear donors for the reconstruction of embryos by nuclear transfer are well known to anyone skilled in the art. Any cell population obtained directly from any stage in the life of an animal (for example, embryo, foetus or adult animal) may be used as a donor genetic material, alternatively a cell from any population may be used (for example an undifferentiated, partially differentiated or differentiated cell population) derived from any stage (for example embryo, foetus, juvenile or adult animal) and maintained in culture or any cell (for example undifferentiated, partially differentiated or differentiated cell) resulting during culture of primary isolates or as a result of treatment of the cultured cell population with hormones, growth factors or chemicals which alter the differentiated state. The cell cycle stage of cells maintained in culture may be manipulated to ensure co-ordination with the recipient cytoplast using any means available to any one skilled in the art. The following examples are non-limiting and are merely representative of various aspects of the art.

G0-Phase

Any method which results in the production of quiescent (non-growing) diploid cells which have arrested the cell cycle following mitosis and cell division but prior to the onset of DNA Replication or S-phase may be used. Suitable methods include but are not restricted to;

I. Quiescence induced by contact inhibition of cultured cell populations
II. Quiescence induced by removal or reduction in concentration of serum or other essential nutrient in the culture medium i.e. leucine or other amino acid, specific growth factor/s.
III. Quiescence induced by senescence
IV. Quiescence induced by addition of a specific growth factor or other substance.
V. Quiescence induced by any physical means such as heat shock, hyperbaric pressure or treatment with chemical compounds which induce a heat shock or stress response e.g puromycin, azacytidine.

G1-Phase

Donor nuclei may be arrested in the G1 phase of the cell cycle by treatment with any chemical, hormone, growth factor or other substance which causes arrest or by any physical stress which induces cell cycle arrest i.e. induction of a heat shock response as a result or elevated temperature or treatment with compounds which induce such a response i.e. puromycin, azacytidine. Alternatively G1 phase cells may be obtained by synchronisation of the cell population by any means and selection of G1 cells at an appropriate time. For example cells may be arrested in the M-phase of the cell cycle by treatment with microtubule disrupting drugs such as Colcemid or Nocodazole, mitotic cells may then be selected from the population by shake-off and placed into a separate culture vessel. G1 cells may then be selected at an appropriate time following shake off. As a variation of this technique, mitotic cells may also be selected from an unsynchronised population. G1 cells may be enriched by causing cells to exit the growth cycle and arrest in a quiescent or G0 phase (as above) and then restimulating growth by re-addition of the restricting factor. G1 cells can then be selected at a time following restimulation to be found by experimentation for each individual cell type/population. This technique may be combined with any technique which then arrests cells in either the G1 phase of the cell cycle, or at the G1/S-phase border i.e. treatment with hydroxyurea or aphidicolin.

S-Phase.

S-phase cells can be selected or enriched for by treatment with any chemical agent which interferes with any point of the replication procedure e.g. aphidicolin which inhibits chain elongation in a concentration dependent manner, Hydroxyurea which inhibits the enzyme ribonucleotide reductase. Cells synchronised in any other stage of the cell cycle may be released and the timing of S-phase after release determined experimentally. In addition these two processes may be combined or any other selection or synchronisation procedure or combination thereof utilised.

G2-Phase

G2 phase cells may be selected from a growing population that has been synchronised by any physical, chemical or selective method. Alternatively G2 cells may be enriched for by treatment of a synchronised or unsynchronised cell population with any agents that specifically arrest the cell cycle following the completion of S-phase and prior to the onset of mitosis.

M-Phase

Mitotic cells may be selected from an unsynchronised population using any means possible including but not being limited to, mitotic shake off, elutriation, FAC's (fluorescence activated cell sorting). Alternatively cells may be arrested in mitosis by treatment with microtubule disrupting agents such as colcemid or nocodazole, by treatment with DMAP or any other serine threonine protein kinase inhibitors or by any other chemical or physical means which disrupts normal growth progression and causes arrest in mitosis.

Unsynchronised Cell Populations.

Unsynchronised cell populations may be obtained from any embryonic foetal or adult tissue and cultured in vitro or any cell removed directly from an embryo, foetus, juvenile or adult animal. An unsynchronised cell is defined as a cell, the cell cycle stage of which is unknown at the time of transfer to a recipient cytoplast.

Nuclear Transfer.

I) Oocytes.

Oocytes to act as suitable cytoplast recipients can be obtained using a variety of techniques and protocols, these include but are not limited to i) In vitro maturation following follicle aspiration from ovaries obtained at slaughter or removed surgically.
ii) Transvaginal follicle puncture followed by maturation in vitro
iii) In vivo matured but collected by transvaginal follicle puncture prior to ovulation, maturation is then completed in vitro.
iv) In vivo matured and surgically recovered.
v) In vivo matured and recovered at slaughter.

It is preferable, but not essential, that all in vivo matured oocytes are harvested by flushing from the oviduct in calcium magnesium free phosphate buffered saline (PBS) (or other suitable medium devoid of calcium and magnesium ions) containing 1.0% foetal calf serum (FCS). Similarly in vitro matured oocytes are harvested and transferred to suitable medium devoid of calcium and magnesium ions (for example M2 medium prepared without addition of calcium and magnesium ions). The chosen medium may be supplemented with FCS, BSA or other protein source. Oocytes are denuded of cumulus cells and enucleated as previously described (Campbell et al., 1993, 1994) with the exception that calcium free medium, although not essential is preferred for all procedures. Fusion procedures are modifications of those previously reported (Campbell et al., 1993, 1994) and are as described in the relevant section below, alternatively the nucleus may be introduced by manual injection of the donor cell into the enucleated oocyte (Ritchie and Campbell, *J. Reproduction and Fertility* Abstract Series No. 15, p 60) or by using a commercially available piezzo injection apparatus as demonstrated in the mouse (Wakayama et al., 1998). The timing of these events is dependent upon the species. The protocols outlined in this application define the use of in vivo and in vitro matured ovine, bovine and porcine oocytes coupled to the use of in vitro or in vivo produced zygotes. The procedure is not limited to these defined protocols.

II) Zygotes.

To act as recipients for the second nuclear transfer fertilised zygotes or oocytes (prior to, concomitant with or following activation) are required. At the present time fertilised zygotes are preferred, although not essential. Matured oocytes may be obtained by any of the procedures outlined above. The genetic material may be removed from the oocyte as previously described. Oocytes may be activated by treating the matured oocytes with any physical or chemical stimulus or combination thereof, which causes activation and stimulates development. The timing of application of the activation stimulus will vary somewhat upon both the species and the method of maturation. Fertilised zygotes may be obtained by in vitro fertilisation of matured oocytes obtained from any of the above sources or alternatively recovered ex vivo following mating or AI using stimulated or non-stimulated donor animals.

First Stage Nuclear Transfer Embryo Reconstruction.

Donor cells at different stages of the cell cycle may be used for embryo reconstruction. The cytoplast recipient used and any additional treatments required will vary somewhat, dependent upon the cell cycle stage of the donor and recipient cells. Table 1 gives a series of possible combinations.

In fact, any method may be used which results in the production of one or more pronucleus-like structure, preferably of normal diploidy or tetraploidy.

Second Stage Nuclear Transfer:

In the second stage of the invention a pronucleus-like structure (preferably identified as a swollen form of the nucleus) from the first nuclear transfer reconstructed embryo is transferred to an enucleated MII (prior to, concomitant with or following activation) or to an activated parthenote or fertilised zygote which have been enucleated by removal of the pronuclei. Although each of these cytoplast recipients are suitable for the second nuclear transfer in practice an enucleated fertilised zygote is the preferred choice. The zygote to act as cytoplast recipient for the second nuclear transfer may be produced in vivo or in vitro, although in practice the use of in vivo produced zygotes is the method of choice at present. Alternatively any cell resulting from development of the first nuclear transfer embryo or cultured cell population derived from this embryo may be used as a donor of genetic material for production of the second nuclear transfer embryo.

Source of Activated Oocyte or Zygote:

Oocytes obtained from any in vitro or in vivo source and subsequently matured in vitro, or oocytes matured in vivo may be used as recipients for the second nuclear transfer following enucleation and subsequent activation or activation and subsequent enucleation. In practice it is preferred that the recipient cytoplast for the second nuclear transfer is prepared from a fertilised zygote. The zygote required for production of a cytoplast recipient for the second nuclear transfer may be obtained from any suitable source which may include but is not limited to; In vivo produced fertilised zygotes that are recovered from a suitable donor animal. Zygotes may be produced by natural mating, by natural mating following superovulation or by AI using fresh or frozen semen. Alternatively, fertilised zygotes may be produced in vitro. In vitro fertilisation may be carried out on oocytes matured in vivo from suitable donors with or without superovulation or by using oocytes matured in vitro following recovery from slaughterhouse material or aspiration of follicles in vivo. In practice it is preferred that the zygote for the second nuclear transfer is obtained following maturation and fertilisation in vivo.

Enucleation of Zygotes.

Following successful fertilisation the male and female chromatin in the newly formed zygote decondenses and forms two pronuclei. The genetic material may be removed at any point following fertilisation. However, in practice the present method of choice is to remove the genetic material after formation of the pronuclei. Due to the nature of the cytoplasm it is often difficult to visualise and remove the pronuclei from a fertilised zygote. Visualisation of the pronuclei may be aided by centrifugation of the zygotes prior to their manipulation, although this is not essential.

Preparation of a Karyoplast Donor from First Nuclear Transfer Embryo

The pronucleus/i formed in the first nuclear transfer reconstructed embryos must be removed and transferred to the second cytoplast recipient. To visualise the pronucleus/i the embryos are preferably centrifuged. Aspiration of a pronucleus surrounded by cytoplasm and enveloped in a cell membrane is then carried out, preferably by microsurgery. To facilitate this process, although not a necessity, the embryo may be rendered more pliable by treatment with one or more chemical compounds, which disrupt the cytoskeleton e.g. Cytochalasin B, or Nocodazole. The centrifuged embryo is preincubated in the agent/s of choice and then transferred to a manipulation chamber. Using a fine glass pipette a karyoplast is aspirated which contains a pronucleus.

Reconstruction of Second Nuclear Transfer Embryo

The karyoplast formed from the first nuclear transfer embryo is used to transfer the genetic material now contained within the pronucleus like structure to the enucleated second recipient cytoplast. Any means of transfer including fusion of the karyoplast to the cytoplast by viral, chemical or electrical means may be used or alternatively the pronucleus may be injected into the recipient cell. Due to the size of the pronucleus it is preferred but not essential that the genetic material is transferred by the process of cell fusion. For cell fusion the karyoplast is transferred below the zona pellucida of the second cytoplast recipient and placed into contact with the enucleated zygote. Any physical, chemical or viral means of inducing cell fusion may then be applied. However, at the present time it is preferable, but not essential, to use electrical fusion. For electrical fusion the couplet is placed into a suitable medium in a suitable fusion chamber. A DC electrical pulse is then passed through the couplet at right angles to the plane of contact between the cytoplast and karyoplast. An AC electrical pulse may first be used to align and/or increase contact between the cytoplast and karyoplast. The duration strength and timing of the electrical pulse/s all affect the frequency of fusion and can be optimised by experimentation.

Culture of Second Nuclear Transfer Embryos.

Following reconstruction of the second nuclear transfer embryo, further development may be carried out by culturing in suitable medium in vitro until a developmental stage suitable for transfer to a final surrogate recipient is reached. Alternatively, reconstructed embryos may be cultured in the ligated oviduct of a suitable, synchronised, intermediate recipient for sufficient time to reach a developmental stage suitable for transfer to a final surrogate recipient. Or as is the method of choice at present in porcine species, the second nuclear transfer reconstructed embryo can be transferred directly to the final surrogate recipient and pregnancy maintained by hormonal treatment (see below).

Transfer to Final Surrogate Recipient

Reconstructed embryos may be cultured by any means in vitro or in vivo to any stage suitable for transfer to a synchronised final recipient for development to term. Alternatively reconstructed embryos may be transferred as soon as possible to a synchronised recipient for development to term. The latter method is presently the method of choice in porcine species. In this situation induction and maintenance of pregnancy in the final recipient can be achieved by either of the following procedures;

At the time of transfer in vivo produced embryos at the same developmental stage as the nuclear transfer reconstructed embryos may be transferred with the nuclear transfer. Alternatively, the recipient may be treated with a combination of hormones in order to maintain pregnancy (Christenson et al., *J. Animal Science* 1971; 32:282-286).

The present invention encompasses genetic modification as known in the art to provide transgenic animals of all stages. The term "transgenic" refers broadly to any animal stage whose germ line has been the subject of technical intervention by recombinant DNA technology. This includes introduction of genetic material from another species as well as an animal in whose germ line an endogenous gene has been deleted, duplicated, activated or modified.

The genetic material (donor nucleus) can be modified at any stage in the double nuclear transfer methodology. Most preferably, the recombinant intervention is carried out before the first nuclear transfer step. The recombinant intervention may be carried out between the first and second nuclear transfer steps.

For recombinant intervention before the first nuclear transfer step, the genetic material is preferably modified as part of a cell line modification or taken from a previously modified animal. A level of selection can be introduced to identify donor nuclei for the nuclear transfer step. Alternatively, or in addition, recombinant intervention can be carried out after the first nuclear transfer step and before the second. In this scenario, the cell obtained may be genetically modified by the same or a different method.

Suitable recombinant technology for genetically modifying nuclear material is well known in the art. It includes methods as discussed and disclosed in WO97/07669, WO97/07668, U.S. Pat. No. 5,612,205, U.S. Pat. No. 5,721,367, WO99/01164, WO99/21415, U.S. Pat. No. 5,945,577 and WO98/37183.

The Present Invention Includes the Use of Unenucleated Oocytes as Cytoplast Recipients for Embryo Reconstruction by Nuclear Transfer.

The development of embryos reconstructed by nuclear transfer is dependent upon many factors that include the cell cycle stage of both the recipient cytoplasm and the donor nucleus. The ability to synchronise the blastomeres of early murine embryos has allowed detailed studies of cytoplast/karyoplast cell cycle combinations. Reports in the mouse have demonstrated the use of mitotically arrested cells as donors of genetic material (Kwon and Kono, *Proc. Natl. Acad. Sci. U.S.A.* 93, 13010-13013). Briefly; blastomeres from nocodazole treated embryos arrested in mitosis are transferred to enucleated MII oocytes. Extrusion of a polar body is inhibited by treatment with cytochalasin B, this results in the formation of two diploid (pro) nuclei. Each of these nuclei is then transferred individually to an enucleated zygote. Using this method, these authors produced 6 identical pups from a single 4-cell embryo. In a further study Otaegui and co-workers (unpublished) the results suggest that during the late G2 and early G1 phase of the donor cell cycle the chromatin is more able to re-direct development. Together these two studies suggest that during late G2, M and early G1 a permissive state exists which allows nuclear reprogramming. One possible explanation for these observations is that during these cell cycle phases, certain factors are displaced from the chromatin as a result of condensation, thus allowing access of oocyte derived factors. This hypothesis is supported by two lines of evidence; firstly, during mitosis, nascent transcripts and transcription factors become displaced from the chromatin (Schermoen, A. W. and O'Farrell, P. H. (1991) *Cell.* 67, 303-310. Martinez-Balbas et al *Cell.* 83, 29-38) and secondly the production of live offspring using mitotically arrested blastomeres as donors of genetic material (Kwon and Kono, *Proc. Natl. Acad. Sci. U.S.A.* 93, 13010-13013).

When using somatic cells as nuclear donors it has been shown that cells arrested in the G0 phase (quiescent) of the cell cycle are able to direct development to term of nuclear transfer reconstructed embryos. The chromatin of quiescent cells has been reported to undergo condensation, these cells also show a reduction in transcription and translation, mRNA is actively degraded and changes occur in the polyribosomes Whitfield, J. F., et al (1985) In 'Control of Animal cell proliferation'. (Eds Boynton A. L. and Leffert, H. L.) pp 331-365. (Academic Press Inc:London.) Quiescent cells reduce their metabolism to that which is required to maintain viability. Conceptually one may expect that the chromatin of cells arrested in G0 and poised to undergo differentiation may be more amenable to respond to a variety of signals. Alternatively, it may merely be a 'more null' state that allows the chromatin to respond to oocyte maternal cytoplasmic factors controlling gene expression after nuclear transfer. This hypothesis is supported by previous observations in the mouse using embryonic blastomeres as nuclear donors (see above). In these reports, donors in late G2-phase M-phase and nuclei in early G1-phase (in which chromatin decondensation is incomplete) have a greater developmental potential than late G1, S or early G2 donors. In these more successful donor nuclei, one can speculate that the release of transcription factors due to chromatin condensation in the donor cell then allows greater access of oocyte cytoplasmic factors as the chromatin decondenses after transfer. Further support for this hypothesis comes from studies in cultured cells which demonstrated that during mitosis, transcription factor binding affinity remains the same but these factors are excluded from the chromatin due to its condensation (Martinez-Balbas et al., *Cell.* 83, 29-38). More recently, other researchers have shown that transcriptionally inactive genes localise to centromeric heterochromatin in the nuclei of cycling but not quiescent primary B-lymphocytes. Stimulation of quiescent cells to re-enter the growth cycle causes repositioning of inactive loci to the centromeric regions (Brown et al, *Mol Cell Biol* 0.3, 207-217). Thus the chromatin of quiescent cells may be more amenable to structural changes after nuclear transfer which are associated with 'reprogramming' of gene expression.

The ability to utilise different cell cycle combinations of donor and recipient cells is dependent upon species. In the mouse, an intact organised spindle is obtained when G2 or M phase nuclei are transferred into enucleated MII oocytes. On activation a "pseudo-mitotic/meiotic" event occurs; a polar body is extruded and a diploid nucleus formed. Alternatively suppression of polar body expulsion by treatment with Cytochalasin B results in a tetraploid embryo with 2 diploid pronuclei. Each of these pronuclei can be used (successfully) as a nuclear donor to an enucleated zygote. In cattle sheep and pigs, following transfer of a nucleus from a diploid (G1) blastomere or a somatic cell into an enucleated MII oocyte, no organised spindle is observed and there are no reports of polar body extrusion suggesting that no organised spindle is in fact formed. Similarly in cattle, when a G2 nucleus is transferred into an enucleated MII oocyte no organised spindle is observed, however if the oocyte is not enucleated 2 organised spindles are observed, one the original oocyte MII and the second organising the chromosomes derived from the donor nucleus.

These differences in spindle organisation can be used to advantage. Nuclei in the G2 or M-phases of the cell cycle can be transferred to a maturing oocyte either I) at a point following metaphase of the first meiotic division i.e. between MI and MII or ii) at MII. At MII there would be 2 spindles present 1 from the maternal DNA and the other from the transferred DNA. Activation of the recipient oocyte can be prevented by methods known in the art i.e. removal of calcium from the culture, manipulation or fusion medium. The transferred chromatin which is condensed into chromosomes may then be allowed to 'be conditioned' in the recipient cytoplasm for a period dependent upon the species and the age of the recipient oocyte. The maternal chromatin may be removed following formation of an intact spindle containing the donor chromatin, or alternatively following activation of the reconstructed oocyte. Activation may be achieved by methods common to the art with the exception that spindle integrity must be maintained. On activation the transferred DNA undergoes a pseudo-mitotic/meiotic division and extrudes a polar body thus giving a diploid embryo. Alternatively the extrusion of the polar body could be prevented with compounds common to the art e.g. Cytochalasin B and the resulting zygote would have 2 diploid pronuclei each of which could be used for transfer to an enucleated zygote or an activated enucleated oocyte.

The original oocyte or maternal DNA could be selectively removed following identification by a number of means 1. By observation of the 1$^{st}$ polar body and aspiration of cytoplasm and the meiotic spindle from directly beneath the polar body prior to activation—this depends on the age of the recipient oocyte as the polar body breaks down on increasing age.
2. Either the maternal or donor chromatin may be selectively stained prior to reconstruction with a DNA specific dye that will then allow selective removal of the stained or unstained chromosomes prior to activation.
3. As in 3 with subsequent removal of the chromosomes or the subsequent pronucleus following activation.
4. By use of transgenic donor cells which contain a specific marker gene driven by a G0 specific promotor sequence.

Examples of the Use of Unenucleated Oocytes

The protocols described for the production of oocytes as recipients for 1$^{st}$ nuclear transfer procedures as described above are all suitable for the use of unenucleated oocytes. Transfer of the donor nucleus can be achieved as previously described using electrical, chemical or virally induced fusion or injection by any means including the use of a piezzo. Enucleation following transfer of the donor nucleus can be achieved by any methods known to the art. The timing of the various procedures will vary between species and be dependent upon the source of oocytes and will be determined experimentally.

The donor cells should be placed in a suitable DNA specific fluorochrome to stain the DNA—i.e. 1 microgram of Hoescht 3332 for 10 minutes in culture medium followed by incubation in medium lacking the stain. Transfer of the nucleus can be carried out at any time after the appearance of telophase of the 1$^{st}$ meiotic division which may be observed microscopically by the appearance of a small protuberance on the cell wall of the oocyte which is well known to those skilled in the art. Manipulation and reconstruction of the recipient oocytes is preferred in a medium that lacks calcium in order to prevent activation. The reconstructed oocytes can then be cultured until the maternal DNA is removed. Sufficient time is allowed for formation of the mitotic spindle (this will vary between species and culture conditions and also on the timing of reconstruction). In the case of Telophase 1 recipients sufficient time is allowed for the oocyte maternal chromatin to reach MII. Enucleation of the maternal chromatin may be achieved at MII by brief exposure to UV light for visualisation and identification of the stained chromatin. Alternatively, the oocytes may be activated and then exposed to UV for identification of the donor chromatin at any time prior to and following pronuclear formation. Following removal of the maternal chromatin and activation the presumptive zygotes are cultured by any means known to the art to a stage suitable for transfer to a synchronised final recipient for development to term.

The unenucleated oocyte is preferably used in the first nuclear transfer step. It may be used in the second.

EXAMPLES

The examples below are non-limiting and are merely representative of various aspects of the present invention.

I) Protocol for Porcine Nuclear Transfer.

Synchronisation Procedure for the Collection of In Vivo Matured Porcine Oocytes.

A suitable procedure for the collection of in vivo matured porcine oocytes is described below. In practice any procedure which results in the production of suitable oocytes may be used.

Feed Altrenogest (Regu-Mate, 18 mg/day, 9 AM) for 5-9 days, starting on day 12-16 of the cycle (day 0 is heat). If no heats are available, feed Altrenogest for 14 days. Inject gilts with Estrumate (1M, 1.0 ml, 9 AM) during the last Altrenogest feeding. Inject eCG (Equine Chorionic Gonadotropin, 1500 IU IM) 14 hrs (11 PM) after the last Altrenogest feeding. Inject hCG (human Chorionic Gonadotropin, 1000 IU, IM) 80 hrs after the eCG injection (7 AM). Collect oocytes 50 hrs after the hCG injection (9 AM).

First Stage Nuclear Transfer Embryo Reconstruction.

A range of protocols are available for the first stage nuclear transfer. Their use is dictated by the cell cycle stage of the donor cell nucleus at the time of transfer.

1. "Magic" (Metaphase Arrested G1/G0 Accepting Cytoplast).

Enucleated oocytes were maintained in calcium free medium 10% FCS at 39° C. In the first stage nuclear transfer it is presently preferred, but not essential, that the donor genetic material is introduced into the enucleated oocyte by piezzo aided injection. To aid injection the cytoplast recipients may be centrifuged at 13,000×G for 5 minutes. The donor cell is placed into medium containing 12% Polyvinyl Pyrollidone (optional), the cell is drawn into the injection pipette and then injected into the oocyte, the cell membrane may be intentionally damaged by selection of an appropriately sized pipette and/or the application of a burst of piezzo vibration and repeated pipetting. The size of the injection pipette is dependent upon the size of the cell. Alternatively, transfer of the nucleus may be achieved by cell fusion. As soon as possible after enucleation a single cell was placed into contact with the oocyte by using a glass pipette to transfer the cell through the hole previously made in the zona pellucida. The cytoplast/cell couplet was then transferred into fusion medium (0.3 M D-Sorbitol supplemented with 0.1 mM Mg SO$_4$ & 0.05 mM CaCl$_2$ in H$_2$O, osmolality 280 mOsM) in the fusion chamber. The couplet was manually aligned between the electrodes. Fusion was induced by application of two DC pulses of 1 kV/cm for 60 μsec at intervals of 5 sec. The couplets were then washed in calcium free medium supplemented with 10% FCS at 37° C. and incubated in the same medium under oil at 37° C. 5% CO$_2$. 30 minutes prior to activation the couplets were transferred to calcium free medium 10% FCS containing 5 μM Nocodazole. Activation was induced as described below, following activation the reconstructed zygotes were incubated in medium NCSU23, 10% FCS at 37° C. 5% CO$_2$ for a further 3 hours. They were then washed 3 times for 5 minutes at 37° C. in the same medium without nocodazole and cultured for a further period of time sufficient for the formation of a pronucleus prior to being used as nuclear donors for the second stage nuclear transfer embryo reconstruction. Alternatively, the donor nucleus may be transferred by either manual or piezzo aided injection or by any other chemical or physical means of producing cell fusion.

2. "Goat" (G0/G1 Activation and Transfer).

Enucleated oocytes were returned to the maturation medium. At 30 or 42 hours post onset of maturation a single cell was placed into contact with the enucleated oocyte. The couplet was transferred to the fusion chamber (see below) in fusion medium 0.3 M D-Sorbitol supplemented with 0.1 mM Mg SO$_4$ & 0.05 mM CaCl$_2$ in H$_2$O, osmolality 280 mOsM. Fusion and activation were induced by application of two DC pulses of 1 kV/cm for 60 μsec at intervals of 5 sec. Couplets were then washed in NCSU23 10% FCS and incubated at 37° C. 5% CO$_2$ for a further period of time sufficient for the formation of a pronucleus prior to being used as nuclear donors for the second stage nuclear transfer embryo reconstruction. Alternatively, the donor nucleus may be transferred by either manual or piezzo aided injection or by any other chemical or physical means of producing cell fusion.

3. "Universal Recipient".

Enucleated oocytes were activated (as described below) and cultured in NCSU23, 10% FCS at 37° C. 5% $CO_2$. After the decay of MPF activity, a single cell was then placed into contact with the oocyte and fusion induced as described below. The couplets were then cultured in NCSU23 10% FCS at 37° C. 5% $CO_2$ for a further period of time sufficient for the formation of a pronucleus prior to being used as nuclear donors for the second stage nuclear transfer embryo reconstruction. Alternatively, the donor nucleus may be transferred by either manual or piezzo aided injection or by any other chemical or physical means of producing cell fusion.

Preparation of a Cytoplast for the Second Nuclear Transfer Embryo Reconstruction.

A suitable cytoplast may be prepared by activation of an enucleated oocyte as described in the 'UNIVERSAL RECIPIENT'. Alternatively, as is preferred at present, a cytoplast recipient may be prepared from any in vivo or in vitro produced zygote. After pronuclear formation the zygote may be centrifuged, in a suitable buffered medium, at 13.000×g for 5 minutes, this aids visualisation of the pronuclei but is not essential. The centrifuged zygotes are placed into the manipulation chamber in a suitable medium (as above) and a portion of cytoplasm containing the two pronuclei aspirated using a micropipette.

Second Stage Nuclear Transfer Embryo Reconstruction.

Synchronisation Procedure for the Collection of In Vivo Fertilised 1-Cell Porcine Zygotes.

A suitable procedure for the collection of in vivo matured porcine oocytes is described below. In practice any procedure which results in the production of suitable oocytes may be used.

Feed Altrenogest (Regu-Mate, 18 mg/day, 9 AM) for 5-9 days, starting on d 12-16 of the cycle (day 0 is heat). If no heats are available, feed Altrenogest for 14 days. Inject gilts with Estrumate (1M, 1.0 ml, 9 AM) during the last Altrenogest feeding. Inject eCG (Equine Chorionic Gonadotropin, 1500 IU IM) 14 hrs (11 PM) after the last Altrenogest feeding. Inject hCG (human Chorionic Gonadotropin, 1000 IU, IM) 79 hrs after the eCG injection (6 AM). Artificially inseminate 24 and 36 hrs after hCG injection. Collect embryos 50 hrs after the hCG injection (noon).

Reconstruction of the Second Stage Nuclear Transfer Embryo.

The karyoplast formed by aspiration of the pronucleus surrounded by a portion of cytoplasm and membrane bound from the first nuclear transfer embryo is placed below the zona pellucida of the second recipient cytoplast in contact with the cytoplast. Fusion of the karyoplast and cytoplast are carried out as below or by any other means. Alternatively the karyoplast, the pronucleus or the pronucleus surrounded by a portion of cytoplasm may be injected into the second nuclear transfer embryo.

Culture of Reconstructed Embryos.

Reconstructed embryos may be cultured in vitro using any suitable culture medium and conditions e.g. NCSU medium supplemented with 10% FCS 37° C. in a humidified atmosphere of 5.0% $CO_2$. Alternatively, as is presently the method of choice in porcine species the reconstructed embryos may be transferred directly to a synchronised final recipient for development to term. The transfer of embryos to a synchronised recipient has been determined to support good embryo and foetal development. In control experiments porcine zygotes were sham manipulated to mimic the zona pellucida damage occurring during the nuclear transfer procedure. These manipulated embryos were then transferred to a suitable recipient. Subsequently the recipient was sacrificed and development of the transferred embryos assessed (table 2).

TABLE 2

Embryo development and pregnancy induction using in vivo derived micromanipulated porcine zygotes. Two holes were made by enucleation pipette in zona pellucida to mimic nuclear transfer micromanipulation. The embryos were then transferred to the recipients.

| No. of transferred "manipulated" 1 cell embryos | Results |
| --- | --- |
| 48 | 26 compacted morulae, and 15 16-cell embryos were collected on Day 6. They were cultured in NCSU-23 for 24 hrs. 29 embryos developed to blastocyst stage. |
| 34 | Open—Slaughter/Pregnancy Check (SPC) on day 21 |
| 35 | Pregnant, SPC on day 21. Four fetuses and 5 reabsorbtion sites were observed. No corpus luteus (CL's), new follicles were present. Pregnancy would be lost. |

Manipulated embryos were able to develop to blastocysts and healthy foetuses.

Fusion and Activation

For activation, oocytes were placed between two parallel electrodes in activation medium 0.3 M D-Sorbitol supplemented with 0.1 mM Mg $SO_4$ & 0.05 mM $CaCl_2$ in $H_2O$, osmolality 280 mOsM. Activation was induced by application of two DC pulses of 1 kV/cm for 60 μsec at intervals of 5 sec. This activation procedure promotes development of parthenogenetic embryos to the blastocyst stage (see Table 3). However, any other suitable medium may be used for example 0.3 M mannitol, 0.1 mM $MgSO_4$, 0.001 mM $CaCl_2$ in distilled water (Willadsen, 1986). Any suitable activation pulse may be used for instance 1 DC pulse of 1.25 kV/cm for 80 μs. For fusion manipulated embryos were treated in a similar manner with the addition that the contact surface between the enucleated oocyte and the cell was arranged parallel to the electrodes. Fusion was induced by application of an AC. current of 3V for 5 seconds followed by DC pulses of 1.0 kV/cm for 60 μs at 5 second intervals.

TABLE 3

Development to the blastocyst stage of porcine oocytes electrically activated at different ages.

| Oocyte age. Hrs post hCG | 51.5 hrs (%) | 54 hrs (%) | 57 hrs (%) | 60 hrs (%) |
| --- | --- | --- | --- | --- |
| 1 experiment | 1/13 (8) | 0/13 | 0/13 (0) | 2/14 (14) |
| 2 experiment | 7/16 (44) | 5/16 (31) | 8/16 (50) | 8/16 (50) |
| Average | 8/29 (28) | 5/29 (17) | 8/29 (28) | 10/30 (33) |

Embryo Culture and Assessment (all Groups)

Following reconstruction embryos may be cultured by a variety of techniques known to those skilled in the art including; in vitro culture in a suitable medium or in vivo culture in the ligated oviduct of a suitable recipient host until a stage for transfer to a final surrogate recipient. Alternatively, as is presently the method of choice in porcine species although not essential, the second stage reconstructed embryos may be transferred directly to the oviduct of a suitable synchronised final recipient host for development to term (see tables 4 and 5).

TABLE 4

Development of double nuclear transfer porcine embryos. first stage nuclear embryos were reconstructed by pizzo injection of diploid primary fibroblasts into in vivo matured enucleated porcine oocyte. second stage nuclear transfer used in vivo produced porcine zygotes. Reconstructed embryos were transferred to the oviduct of a synchronised recipient sow and recovered on day 6 to assess development

| Group | Number attempted fusions | Number Lysed (%) | Number Fused (%) | Number of Blastocysts (%) |
|---|---|---|---|---|
| 1 | 23-fusions | 0 (0) | 13/23 (57) | 4 (31) |

TABLE 5

Pregnancy outcome following transfer of double nuclear transfer embryos directly to a synchronised final recipient.

| Replicate | Number Of Embryos Transferred | Pregnancy And Comments |
|---|---|---|
| 1 | 48 | Pregnant d28, open d34 |
| 2 | 4 | Open d28, Open d35 |
| 3 | 4 | Open d28, Open d35 |
| 4 | 9 | Not tested |

Synchronisation Procedure for the Preparation of Surrogate Recipients for Nuclear Transfer Reconstructed Embryos.

Same method as used for the preparation of zygotes with the following differences, no eCG, no AI and 1.5 days behind.

Procedure for the Maintenance of Pregnancy in Surrogate Recipients.

In order to maintain pregnancy in the final recipient in vivo produced embryos at the same developmental stage as the reconstructed embryos may be transferred with the nuclear transfer embryos. Alternatively, as is presently preferred in porcine species the final recipient may be treated hormonally to maintain pregnancy in the following manner, eCG (1000 IU) on day 9 or day 10 of pregnancy, hCG (500 IU) 3 to 3.5 days later.

II) Protocol for Ovine Nuclear Transfer:

Materials and Methods.

Superstimulation of Donor Ewes and Recovery of Oocytes.

Scottish Blackface ewes were synchronised with progestagen sponges for 14 days (Veramix, Upjohn, UK) and induced to superovulate with single injections of 3.0 mg/day (total 6.0 mg) ovine follicle-stimulating hormone (FSH) (Ovagen, Immuno-chemical Products Ltd. New Zealand) on two successive days. Ovulation was induced with an 8 mg single dose of a gonadotropin-releasing hormone analogue (GnRH Receptal, Hoechst. UK.) 24 hours after the second injection of FSH. Unfertilised metaphase II oocytes were recovered by flushing from the oviduct at 24-29 hours after GnRH injection using Dulbecco's phosphate buffered saline containing 1.0% foetal calf serum (FCS) maintained at 37° C. until use.

Oocyte Manipulation.

Recovered oocytes were maintained at 37° C., washed in PBS 1.0% FCS and transferred to calcium free M2 medium containing 10% Foetal Calf Serum (FCS), at 37° C. To remove the chromosomes (enucleation) oocytes were placed in calcium free M2 containing 10% FCS, 7.5 ug/ml Cytochalasin B (Sigma) (Cytochalasin B is optional) and 5.0 ug/ml Hoechst 33342 (Sigma) at 37° C. for 20 minutes. A small amount of cytoplasm from directly beneath the first polar body was then aspirated using a 20 µM glass pipette. Enucleation was confirmed by exposing the aspirated portion of cytoplasm to UV light and checking for the presence of a metaphase plate.

First Stage Nuclear Transfer Embryo Reconstruction.

A range of protocols are available for the first stage nuclear transfer. Their use is dictated by the cell cycle stage of the donor cell nucleus at the time of transfer.

Embryo Reconstruction.

Groups of 10-20 oocytes were enucleated and placed into 20 µl drops of calcium free M2 medium at 37° C. 5% $CO_2$ under mineral oil (SIGMA). Three protocols were used for embryo reconstruction.

1. "Magic" (Metaphase Arrested G1/G0 Accepting Cytoplast).

As soon as possible after enucleation a single cell was placed into contact with the oocyte by using a glass pipette to transfer the cell through the hole previously made in the zona pellucida. The cytoplast/cell couplet was then transferred into the fusion chamber in 200 µl of 0.3M mannitol in distilled water. and manually aligned between the electrodes. An AC pulse of 5V was applied for 3 seconds followed by 3 D.C. pulses of 1.25 kV/cm for 80 µsecs. The couplets were then washed in calcium free M2, 10% FCS at 37° C. and incubated in the same medium under oil at 37° C. 5% $CO_2$. 30 minutes prior to activation the couplets were transferred to calcium free M2 medium 10% FCS containing 5 µM Nocodazole. Activation was induced at 32-34 hours post hCG injection as described below. Following activation the reconstructed zygotes were incubated in medium TC199 10% FCS at 37° C. 5% $CO_2$ for a further 3 hours. They were then washed 3 times for 5 minutes at 37° C. in the same medium without nocodazole and cultured for a further period of time sufficient for the formation of a pronucleus prior to being used as nuclear donors for the second stage nuclear transfer embryo reconstruction. Alternatively, the donor nucleus may be transferred by either manual or piezzo aided injection or by any other chemical or physical means of producing cell fusion.

2. "Goat" (G0/G1 Activation and Transfer).

At 32-34 hours post hCG injection a single cell was placed into contact with the enucleated oocyte. The couplet was transferred to the fusion chamber (see below) in 200 µl of 0.3 M mannitol, 0.1 mM $MgSO_4$, 0.001 mM $CaCl_2$ in distilled water. Fusion and activation were induced by application of an AC. pulse of 3V for 5 seconds followed by 3 DC. pulses of 1.25 kV/Cm for 80 µsecs. Couplets were then washed in TC199 10% FCS (the addition of 7.5 µg/ml Cytochalasin B to this medium is optional) and incubated in this medium for 1 hour at 37° C. 5% $CO_2$. Couplets were then washed in TC199 10% FCS and cultured in TC199 10% FCS at 37° C. 5% $CO_2$. for a further period of time sufficient for the formation of a pronucleus prior to being used as nuclear donors for the second stage nuclear transfer embryo reconstruction. Alternatively, the donor nucleus may be transferred by either manual or piezzo aided injection or by any other chemical or physical means of producing cell fusion.

3. "Universal Recipient".

Enucleated oocytes were activated (as described below) 32-34 hours post hCG injection and then cultured in TC199

10% FCS at 37° C. 5% $CO_2$ for 4-6 hours. A single cell was then placed into contact with the oocyte and fusion induced as described below. The couplets were then incubated in TC199 10% FCS 7.5 μg cytochalasin B for 1 hour at 37° C. 5% $CO_2$. Couplets were then washed and cultured in TC199 10% FCS at 37° C. 5% $CO_2$ for a further period of time sufficient for the formation of a pronucleus prior to being used as nuclear donors for the second stage nuclear transfer embryo reconstruction. Alternatively, the donor nucleus may be transferred by either manual or piezzo aided injection or by any other chemical or physical means of producing cell fusion.

Second Stage Nuclear Transfer Embryo Reconstruction.

Collection of Zygotes.

Superstimulation of Donor Ewes and Recovery of Oocytes.

Scottish Blackface ewes were synchronised with progestagen sponges for 14 days (Veramix, Upjohn, UK) and induced to superovulate with single injections of 3.0 mg/day (total 6.0 mg) ovine follicle-stimulating hormone (FSH) (Ovagen, Immuno-chemical Products Ltd. New Zealand) on two successive days. Ovulation was induced with an 8 mg single dose of a gonadotropin-releasing hormone analogue (GnRH Receptal, Hoechst. UK.) 24 hours after the second injection of FSH. Unfertilised metaphase II oocytes were recovered by flushing from the oviduct at 24-29 hours after GNRH injection using Dulbecco's phosphate buffered saline containing 1.0% foetal calf serum (PCS) maintained at 37° C. until use. Recovered oocytes were fertilised in vitro using techniques available to those skilled in the art. Alternatively superstimulated ewes were mated or fertilised by artificial insemination using fresh or frozen serum. Fertilised zygotes were recovered surgically by flushing from the oviduct in any suitable medium.

Preparation of a Cytoplast for the Second Nuclear Transfer Embryo Reconstruction.

A suitable cytoplast may be prepared by activation of an enucleated oocyte as described in the 'UNIVERSAL RECIPIENT'. Alternatively, as is preferred at present, a cytoplast recipient may be prepared from any in vivo or in vitro produced zygote. After pronuclear formation the zygote may be centrifuged, in a suitable buffered medium, at 13.000×g for 5 minutes, this aids visualisation of the pronuclei but is not essential. The centrifuged zygotes are placed into the manipulation chamber in a suitable medium (as above) and a portion of cytoplasm containing the two pronuclei aspirated using a micropipette.

Reconstruction of the Second Stage Nuclear Transfer Embryo.

The karyoplast formed by aspiration of the pronucleus surrounded by a portion of cytoplasm and membrane bound from the first nuclear transfer embryo is placed below the zona pellucida of the second recipient cytoplast in contact with the cytoplast. Fusion of the karyoplast and cytoplast are carried out as below or by any other means. Alternatively the karyoplast, the pronucleus or the pronucleus surrounded by a portion of cytoplasm may be injected into the second nuclear transfer embryo.

Fusion and Activation

For activation, oocytes were placed between two parallel electrodes in 200 μl of 0.3 M mannitol, 0.1 mM $MgSO_4$, 0.001 mM $CaCl_2$ in distilled water (Willadsen, 1986). Activation was induced by application of 1 DC pulse of 1.25 kV/cm for 80 μs. For fusion manipulated embryos were treated in a similar manner with the addition that the contact surface between the enucleated oocyte and the cell was arranged parallel to the electrodes. Fusion was induced by application of an AC. current of 3V for 5 seconds followed by 3 DC pulses of 1.25 kV/cm for 80 μs Embryo Culture and Assessment (all Groups)

After the culture period fused couplets were double embedded in 1% and 1.2% agar (DIFCO) in PBS (or any other suitable protective covering material) and transferred to the ligated oviduct of unsynchronised ewes. After 6 days recipient ewes were sacrificed and the embryos retrieved by flushing from the oviduct using PBS 10% FCS. Embryos were dissected from the agar chips using 2 needles and development assessed by microscopy. All embryos which had developed to the morula/blastocyst stage were transferred as soon as possible to the uterine horn of synchronised final recipient ewes. Alternatively the second stage reconstructed embryos may be transferred directly to the oviduct of a suitable synchronised final recipient host for development to term.

III) Protocol for Bovine Nuclear Transfer:

Materials and Methods.

Bovine oocytes and zygotes for use as recipients for nuclear transfer embryo reconstruction may be obtained from any source or by any of the methods available to anyone skilled in the art. The following examples are non-limiting and are merely representative of various aspects of the present invention.

In Vitro Oocyte Maturation

Ovaries were obtained from a local abattoir and maintained at 28-32° C. during transport to the laboratory. Cumulus oocyte complexes (COC's) were aspirated from follicles 3-10 mm in diameter using a hypodermic needle (1.2 mm internal diameter) and placed into sterile plastic universal containers. The universal containers were placed into a warmed chamber (35° C.) and the follicular material allowed to settle for 10-15 minutes before pouring off three quarters of the supernatant. The remaining follicular material was diluted with an equal volume of dissection medium (TCM 199 with Earles salts (Gibco), 75.0 mg/l kanamycin, 30.0 mM Hepes, pH7.4, osmolarity 280 mOsmols/Kg $H_2O$) supplemented with 10% bovine serum, transferred into an 85 mm petri dish and searched for COC's under a dissecting microscope. Complexes with at least 2-3 compact layers of cumulus cells were selected washed three times in dissection medium and transferred into maturation medium (TC medium 199 with Earles salts (Gibco), 75 mg/l kanamycin, 30.0 mM Hepes, 7.69 mM $NaHCO_3$, pH7.8, osmolarity 280 mOsmols/Kg $H_2O$) supplemented with 10% bovine serum and $1 \times 10^6$ granulosa cells/ml and cultured until required on a rocking table at 39° C. in an atmosphere of 5% $CO_2$ in air.

Oocyte Manipulation.

Matured oocytes were stripped of cumulus cells 18 hours after the onset of maturation. Denuded oocytes were then washed in calcium free M2 medium containing 10% Foetal Calf Serum (FCS) and maintained in this medium at 37° C. To remove the chromosomes (enucleation) oocytes were placed in calcium free M2 containing 10% FCS, 7.5 ug/ml Cytochalasin B (Sigma) and 5.0 ug/ml Hoechst 33342 (Sigma) at 37° C. for 20 minutes. A small amount of cytoplasm from directly beneath the first polar body was then aspirated using a 20 μM glass pipette. Enucleation was confirmed by exposing the aspirated portion of cytoplasm to UV light and checking for the presence of a metaphase plate. Enucleated oocytes were then used for each of the three methods of reconstruction as detailed below.

First Stage Nuclear Transfer Embryo Reconstruction.

A range of protocols are available for the first stage nuclear transfer. Their use is dictated by the cell cycle stage of the donor cell nucleus at the time of transfer.

1. "Magic" (Metaphase Arrested G1/G0 Accepting Cytoplast).

Enucleated oocytes were maintained in calcium free M2 10% FCS at 39° C. as soon as possible after enucleation a single cell was placed into contact with the oocyte by using a glass pipette to transfer the cell through the hole previously made in the zona pellucida. The cytoplast/cell couplet was then transferred into the fusion chamber in 200 μl of 0.3M mannitol in distilled water. The couplet was manually aligned between the electrodes. An AC pulse of 3V was applied for 5 seconds followed by 3 D.C. pulses of 1.25 kV/cm for 80 μsecs. The couplets were then washed in calcium free M2, 10% FCS at 37° C. and incubated in the same medium under oil at 37° C. 5% $CO_2$. 30 minutes prior to activation the couplets were transferred to calcium free M2 medium 10% FCS containing 5 μM Nocodazole. Activation was induced as described below, following activation the reconstructed zygotes were incubated in medium TC199 10% FCS at 37° C. 5% $CO_2$ for a further 3 hours. They were then washed 3 times for 5 minutes at 37° C. in the same medium without nocodazole and cultured for a further period of time sufficient for the formation of a pronucleus prior to being used as nuclear donors for the second stage nuclear transfer embryo reconstruction. Alternatively, the donor nucleus may be transferred by either manual or piezzo aided injection or by any other chemical or physical means of producing cell fusion.

2. "Goat" (G0/G1 Activation and Transfer).

Enucleated oocytes were returned to the maturation medium. At 30 or 42 hours post onset of maturation a single cell was placed into contact with the enucleated oocyte. The couplet was transferred to the fusion chamber (see below) in 200l of 0.3 M mannitol, 0.1 mM $MgSO_4$, 0.001 mM $CaCl_2$ in distilled water. Fusion and activation were induced by application of an AC. pulse of 3V for 5 seconds followed by 3 DC. pulses of 1.25 kV/Cm for 80 μsecs. Couplets were then washed in TC199 10% FCS and incubated at 37° C. 5% $CO_2$ for a further period of time sufficient for the formation of a pronucleus prior to being used as nuclear donors for the second stage nuclear transfer embryo reconstruction. Alternatively, the donor nucleus may be transferred by either manual or piezzo aided injection or by any other chemical or physical means of producing cell fusion.

3. "Universal Recipient".

Enucleated oocytes were activated (as described below) 30 or 42 hours post onset of maturation and then cultured in TC199 10% FCS at 37° C. 5% $CO_2$ for 8-10 hours (30 hpm group) or 4-6 hours (42 hpm group). A single cell was then placed into contact with the oocyte and fusion induced as described below. The couplets were then cultured in TC199 10% FCS at 37° C. 5% $CO_2$ for a further period of time sufficient for the formation of a pronucleus prior to being used as nuclear donors for the second stage nuclear transfer embryo reconstruction. Alternatively, the donor nucleus may be transferred by either manual or piezzo aided injection or by any other chemical or physical means of producing cell fusion.

Second Stage Nuclear Transfer Embryo Reconstruction.

Preparation of a Cytoplast for the Second Nuclear Transfer Embryo Reconstruction.

A suitable cytoplast may be prepared by activation of an enucleated oocyte as described in the 'UNIVERSAL RECIPIENT'. Alternatively, as is preferred at present, a cytoplast recipient may be prepared from any in vivo or in vitro produced zygote. After pronuclear formation the zygote may be centrifuged, in a suitable buffered medium, at 13.000×g for 5 minutes, this aids visualisation of the pronuclei but is not essential. The centrifuged zygotes are placed into the manipulation chamber in a suitable medium (as above) and a portion of cytoplasm containing the two pronuclei aspirated using a micropipette.

Reconstruction of the Second Stage Nuclear Transfer Embryo.

The karyoplast formed by aspiration of the pronucleus surrounded by a portion of cytoplasm and membrane bound from the first nuclear transfer embryo is placed below the zona pellucida of the second recipient cytoplast in contact with the cytoplast. Fusion of the karyoplast and cytoplast are carried out as below or by any other means. Alternatively the karyoplast, the pronucleus or the pronucleus surrounded by a portion of cytoplasm may be injected into the second nuclear transfer embryo.

Fusion and Activation

For activation, oocytes were placed between two parallel electrodes in 200 μl of 0.3 M mannitol, 0.1 mM, $MgSO_4$, 0.001 mM $CaCl_2$ in distilled water (Willadsen, 1986). Activation was induced by application of 1 DC pulse of 1.25 kV/cm for 80 μs. For fusion manipulated embryos were treated in a similar manner with the addition that the contact surface between the enucleated oocyte and the cell was arranged parallel to the electrodes. Fusion was induced by application of an AC. current of 3V for 5 seconds followed by 3 DC pulses of 1.25 kV/cm for 80 μs.

Embryo Culture and Assessment (all Groups)

After the second stage nuclear transfer fused couplets were double embedded in 1% and 1.2% agar (DIFCO) in PBS and transferred to the ligated oviduct of synchronised or unsynchronised ewes. After 6 days recipient ewes were sacrificed and the embryos retrieved by flushing from the oviduct using PBS 10% FCS. Embryos were dissected from the agar chips using 2 needles and development assessed by microscopy. Alternatively the second stage reconstructed embryos may be transferred directly to the oviduct of a suitable synchronised final recipient host for development to term.

TABLE 1

Possible cell cycle combinations of donor and recipient cells for first NT in order to maintain ploidy of the nucleus/i of the reconstructed zygotes.

| DONOR CELL CYCLE STAGE | RECIPIENT CYTOPLAST | OTHER TREATMENT |
|---|---|---|
| G0 | MII CONCOMITANT with ACTIVATION | |
| G0 | MII POST-ACTIVATION | CHEMICAL MAINTENANCE OF PLOIDY (i.e. Nocodazole, Colcemid, DMAP or other serine threonine kinase inhibitors). |
| G0 | MII PRE-ACTIVATION | |
| G1 | MII CONCOMITANT with ACTIVATION | |
| G1 | MII POST-ACTIVATION | CHEMICAL MAINTENANCE OF PLOIDY (i.e. Nocodazole, Colcemid, DMAP or other serine threonine kinase inhibitors). |
| G1 | MII PRE-ACTIVATION | |
| S | PRE-ACTIVATION | |

TABLE 1-continued

Possible cell cycle combinations of donor and recipient cells for first NT in order to maintain ploidy of the nucleus/i of the reconstructed zygotes.

| DONOR CELL CYCLE STAGE | RECIPIENT CYTOPLAST | OTHER TREATMENT |
|---|---|---|
| G2 | MII enucleated POST-ACTIVATION | Tetraploid PN Transfer to late G2/mitotic 1 cell zygote |
| G2 | MII unenucleated POST-ACTIVATION | Subsequent enucleation *Suppression of PB formation if required to form 2 diploid pronuclei |
| G2 | MII PRE-ACTIVATION | |
| S | MII PRE-ACTIVATION | |
| M | MII enucleated POST-ACTIVATION | Depolymerisation of spindle if required i.e nocodazole to form a single tetraploid pronucleus. Transfer to late G2/mitotic 1 cell zygote |
| M | MII enucleated PRE-ACTIVATION LATE G2 (MPF rising or high) | |
| M | MII enucleated POST-ACTIVATION | Tetraploid PN Transfer to late G2/initotic 1 cell zygote |
| M | MII unenucleated POST-ACTIVATION | Subsequent enucleation *Suppression of PB formation if required to form 2 diploid pronuclei |

*Dependent upon species.

IV. Generation of Cloned Pigs Using Somatic Cells as Nuclear Donors.

Isolation of Porcine Granulosa Cells:

Granulosa cells were harvested from ovarian follicles by needle aspiration of follicular fluid. Animals from which ovaries were collected were prepared identically to those used for oocyte collection (see Oocyte recovery below). Follicles were aspirated by penetrating through the cortex of the ovary using an 18 gauge hypodermic needle attached to a 10 ml syringe. Follicular fluid was collected from follicles between 2 and 5 mm in diameter, was placed into a 15 ml conical centrifuge tube, and centrifuged at 1000 rpm for 10 min. The cell pellet was re-suspended into DMEM (Gibco), containing 10% FCS (Summit Biotech), NEAA, 2 ng/ml bFGF and 6 µl/ml gentamycin. Cells were expanded for several days and then cryopreserved.

Preparation of Cells for Nuclear Transfer.

Donor cells were plated at $1-5\times10^4$ cells per 35 mm dish and were allowed to reach 100% confluency in DMEM medium supplemented with NEAA (0.1 mM), bFGF (2 ng/ml), and 10% fetal calf serum. Contact inhibition was chosen for cell synchronization in order to maximize the number of healthy cells with a diploid DNA content. See cell cycle data for details.

Cells were harvested by trypsinisation and stored in suspension in a calcium-free phosphate buffered version of NCSU-23 medium at 38.5° C. for 20-120 minutes, prior to use as nuclear donors.

Cell Cycle Analysis (Granulosa Cells)

Since MII oocytes were used as recipient cytoplasts for the first step of nuclear transfer (NT), donor cells having a diploid DNA content were chosen to maintain the appropriate coordination of ploidy of the resultant reconstructed embryo. The position within the cell cycle of various populations of cells after 8 days of culture, was determined by measuring the DNA content using flow cytometry. Three populations were analyzed: sub-confluent actively growing granulosa cells, contact inhibited granulosa cells, and granulosa cells serum starved for 48 hours.

The results of this experiment are summarized in Table 6. It was observed that following serum starvation, the granulosa cell population contained a large proportion (7.2%) of structures having a DNA content lower than that consistent with a cell in G1 (they were sub-G1). These structures are characteristic of cells undergoing apoptosis and senescence, and thus indicated that the granulosa cells did not tolerate serum starvation very well. Synchronization of the cells by contact inhibition (100% confluent) was more effective, given that a higher proportion of cells were in G1/G0 (90.3%), and there were fewer apoptotic sub-G1 cells in the population (only 1.6%).

TABLE 6

Cell cycle analysis of granulosa cells. Values are expressed as the percentage of the total number of cells in the population.

| Stage Of Cell Cycle | Non-Starved | Serum Starved | 100% Confluent |
|---|---|---|---|
| G1/G0 | 78.8 | 82.3 | 90.3 |
| S | 3.7 | 1.9 | 2.2 |
| G2/M | 13.9 | 6.7 | 4.5 |
| Sub G1 | 0.7 | 7.2 | 1.6 |

Synchronization and Superovulation of Gilts for Oocyte and Zygote Recovery

Oocyte Recoveries.

Crossbred gilts (280-320 lbs.) were synchronized, superovulated and oocytes were collected. Gilts were synchronized by oral administration of 18-20 mg Regu-Mate (Altrenogest, Hoechst) mixed into the feed. Regu-Mate was fed for 5-14 days using a scheme that is dependent on the stage of the estrous cycle. Estrumate (250 µg, Bayer) was administered IM the last day of the Regu-Mate treatment. Superovulation was induced with a 1600 IU IM injection of Pregnant Mare Serum Gonadotropin (PMSG, Diosynth) 15-17 hours after the last Regu-Mate feeding. 1500 units of human Chorionic Gonadotropin (hCG, Intervet America) were administered IM 82 hours after the PMSG injection. Oocytes were collected 50-52 hours after the hCG injection using Dulbecco's phosphate buffered saline containing BSA (4 g/l).

Pregnancy Maintenance

Pregnancy was maintained by using a combination of Pregnant Mare Serum Gonadotropin (PMSG) and Human Chorionic Gonadotropin (hCG). PMSG (1000 IU) was injected IM on d10 of the estrous cycle, dl being the day of estrus. Human Chorionic Gonadotropin was injected IM 3 to 3.5 days later, on d13 of the cycle.

Zygote Recoveries.

Crossbred gilts (280-320 lbs.) were synchronized, superovulated and zygotes were collected. Gilts were synchronized by oral administration of 18-20 mg Regu-Mate (Altrenogest, Hoechst) mixed into the feed. Regu-Mate was fed for 5-14 days; dependent on the stage of the estrous cycle the gilts were in. Estrumate (250 g, Bayer) was administered IM the last day of the Regu-Mate treatment. Superovulation was induced by a 1600 IU IM injection of Pregnant Mare Serum Gonadotropin (PMSG, Diosynth) 15-17 hours after the last Regu-Mate feeding. 1500 units of Human Chorionic Gonadotropin (hCG, Intervet America) were administered 78 hours after the PMSG injection. The gilts were then either artificially inseminated or bred naturally 24-36 hours after the hCG injection. Zygotes were collected 52-54 hours after the hCG injection using Dulbecco's phosphate buffered saline containing BSA (4 g/l).

Oocyte Enucleation.

Recovered oocytes were maintained at 38° C., washed in phosphate buffered saline (PBS) with 4 g/l BSA and transferred to calcium free phosphate buffered NCSU-23 medium, at 38° C. To remove the chromosomes (enucleation) oocytes were first placed in calcium free phosphate buffered NCSU-23 medium containing 5 μg/ml Cytochalasin B (Sigma) (Cytochalasin B is optional) and 7.5 μg/ml Hoechst 33342 (Sigma) at 38° C. for 20 minutes. A small amount of cytoplasm from directly beneath the 1st polar body was then aspirated using a 18 μM glass pipette. Enucleation was confirmed by exposing the aspirated portion of cytoplasm in the pipette to UV light, and checking for the presence of a metaphase plate.

Embryo Reconstruction (Day 1).

Groups of 10-20 oocytes were enucleated and placed into 20 μl drops of calcium free phosphate buffered version of the NCSU-23 medium at 38° C. under mineral oil (SIGMA). At 53-56 hours post hCG injection, a single cell was placed under the zona pellucida in contact with the enucleated cytoplasm. The couplet was transferred to a fusion chamber (model #BT-453, BTX Inc. San Diego, Calif.) containing 700 μl of 0.3 M mannitol, 0.1 mM $MgSO_4$, 0.1 mM $CaCl_2$ in deionized water. Fusion and activation were induced by application of an AC pulse of 5V for 5 seconds followed by 2 DC pulses of 1.5 kV/Cm for 60 μsec using an ECM2001 Electrocell Manipulator (BTX Inc., San Diego, Calif.). Couplets were then washed in bicarbonate buffered NCSU-23 medium, and incubated in this medium for 0.5-1 hour at 38.6° C. in a humidified atmosphere consisting of 5% $CO_2$ in air. Couplets were then checked for fusion at 300× magnification using an inverted microscope. Fused reconstructed embryos were artificially activated using 2 successive DC pulses of 1.2 kV/cm for 60 μsec each, and cultured overnight.

Double Nuclear Transfer (Second day)

The double nuclear transfer procedure refers to the reconstruction of enucleated zygotes on day 2, using nuclei produced by day 1 nuclear transfer.

Assessment of nuclear formation from previous day (day 1) of nuclear transfer Reconstructed embryos from previous day of nuclear transfer were removed from culture and centrifuged in a Biofuge at 13,000 rpm for 15 min to observe nucleus formation. Embryos were evaluated for the presence of a pseudo-pronucleus by observation at 300× using an inverted microscope. Embryos with a pseudo-pronucleus were sorted, counted, and placed back in an NCSU-23-containing culture plate in an incubator at 38.6° C., with 5% $CO^2$ in air.

Zygote Enucleation:

Zygotes were centrifuged at 13,000 rpm for 15 min in Biofuge 13 centrifuge. The zygotes were then placed in phosphate buffered NCSU-23 medium containing 5.0 μg/ml Cytochalasin B (Sigma) at 38° C., and incubated for 20 minutes incubated for 20 minutes. Fertilized zygotes with 2 pronuclei were used for enucleation.

To remove the nuclei, an enucleation pipette (25-35 μm) was inserted through the zona pelucida and into the cytoplasm, so that the opening of the enucleation pipette was close to the pronuclei. Both pronuclei and the polar bodies were aspirated by slowly applying negative pressure on the enucleation line.

Reconstruction of Enucleated Zygotes:

Day 1 reconstructed embryos were placed into phosphate buffered NCSU-23 medium containing Cytochalasin B and Nocodazole. A 30-45 μm enucleation pipette was used for manipulation. Karyoplasts were prepared by aspirating the psuedo-pronucleus with minimal surrounding cytoplasm. These karyoplast were slowly expeled into the perivitelline space of enucleated zygotes. The couplets were transferred to the fusion chamber containing 700 μl of SOR2 medium. Fusion was induced by application of an AC pulse of 5V for 5 seconds followed by 2 DC pulses of 1.2 kV/cm for 60 μsec. Couplets were then washed with NCSU-23 medium, incubated in this medium for 0.5-1 hour at 38.6° C., 5% $CO_2$, and then checked for fusion. Fused couplets were transferred as soon as possible to the oviduct of an estrus-synchronized recipient gilt. Results of nuclear transfer using primary granulosa cells are summarized in Table 7.

TABLE 7

| Nuclear transfer using porcine granulosa cells | |
|---|---|
| No. reconstructed embryos-Day 1 | 196 |
| No. fused embryos-Day 1 (%) | 124/183 (68) |
| No. reconstructed embryos-Day 2 | 74 |
| No. fused embryos-Day 2 (%) | 72/74 (97) |
| No. embryos transferred to recipient | 72 |
| No. fetuses detected at day 29 by ultrasound scan | 3[1] |
| No. fetuses detected at day 42 by ultrasound scan | 2[2] |

[1]at least 3 fetuses; [2]at least 2 fetuses. It was difficult to determine the exact number of the fetuses by ultrasound in pigs due to the anatomical position of the pig uterus. Ultrasound images confirmed the pregnancies at day 29 and day 42 of gestation.

Protocol for Bovine Nuclear Transfer:

Materials and Methods.

Bovine oocytes and zygotes for use as recipients for nuclear transfer embryo reconstruction may be obtained from any source or by any of the methods available to anyone skilled in the art. The following examples are non-limiting and are merely representative of various aspects of the present invention.

In Vitro Oocyte Maturation

Ovaries were obtained from a local abattoir and maintained at 28-32° C. during transport to the laboratory. Cumulus oocyte complexes (COC's) were aspirated from follicles 3-10 mm in diameter using a hypodermic needle (1.2 mm internal diameter) and placed into sterile plastic universal containers. The universal containers were placed into a warmed chamber (35° C.) and the follicular material allowed to settle for 10-15 minutes before pouring off three quarters of the supernatant. The remaining follicular material was diluted with an equal volume of dissection medium (TCM 199 with Earles salts (Gibco), 75.0 mg/l kanamycin, 30.0 mM Hepes, pH7.4, osmolarity 280 mOsmols/Kg $H_2O$) supplemented with 10% bovine serum, transferred into an 85 mm petri dish and searched for COC's under a dissecting microscope. Complexes with at least 2-3 compact layers of cumulus cells were selected washed three times in dissection medium and transferred into maturation medium (TC medium 199 with Earles salts (Gibco), 75 mg/l kanamycin, 30.0 mM Hepes, 7.69 mM $NaHCO_3$, pH7.8, osmolarity 280 mOsmols/Kg $H_2O$) supplemented with 10% bovine serum and $1 \times 10^6$ granulosa cells/ml and cultured until required on a rocking table at 39° C. in an atmosphere of 5% $CO_2$ in air. Early during maturation 13 hours post onset the oocytes were placed into medium containing Hoescht 3332 (Sigma) 1 µg/ml for 10 minutes, washed 3 times in maturation medium without Hoescht and returned to maturation. Alternatively the donor cells were exposed to growth medium containing Hoescht 3332) 1 µg/ml for 10 minutes then washed 3 times in growth medium and stored in culture medium until use.

Oocyte Manipulation.

Matured oocytes were stripped of cumulus cells 18 hours after the onset of maturation. Denuded oocytes were then washed in calcium free M2 medium containing 10% Foetal Calf Serum (FCS) and maintained in this medium at 37° C.

Unenucleated Oocyte Reconstruction.

oocytes were maintained in calcium free M2 10% FCS at 39° C. a single cell was placed into contact with the oocyte by using a glass pipette to transfer the cell through the hole previously made in the zona pellucida. The cytoplast/cell couplet was then transferred into the fusion chamber in 200 µl of 0.3M mannitol in distilled water. The couplet was manually aligned between the electrodes. An AC pulse of 3V was applied for 5 seconds followed by 3 D.C. pulses of 1.25 kV/cm for 80 µsecs. The couplets were then washed in calcium free M2, 10% FCS at 37° C. and incubated in the same medium under oil at 37° C. 5% $CO_2$ for 60 minutes. Fusion was assessed microscopically. Fused couplets were placed into maturation medium for 2-20 hours. Alternatively, the donor nucleus may be transferred by either manual or piezzo aided injection or by any other chemical or physical means of producing cell fusion.

Enucleation:

1. Fused oocytes were incubated as described above. Following incubation the maternal chromatin was removed. To remove the chromosomes (enucleation) oocytes were placed in calcium free M2 containing 10% FCS at 37° C. If the $1^{st}$ polar body was visible a small amount of cytoplasm from directly beneath the $1^{st}$ polar body was then aspirated using a 20 µM glass pipette. If the polar body was not visible the oocyte was exposed briefly 1-2 seconds to UV light to identify the stained donor (or oocyte) chromatin.

2. At 24-45 hours post onset of maturation oocytes were activated as described below. 30-60 minutes following activation (or sufficient time for telophase to occur) the relevant chromatin was identified by brief exposure to UV light and removed by aspiration 3. At 24-45 hours following the onset of maturation, activation was induced as described below, following activation the reconstructed zygotes were incubated in medium TC199 10% FCS at 37° C. 5% $CO_2$ for a further period of time sufficient for the formation of a pronucleus. The relevant pronucleus was identified by brief exposure to UV light and aspirated Enucleated oocytes were returned to the maturation medium. At 30 or 42 hours post onset of maturation a single cell was placed into contact with the enucleated oocyte. The couplet was transferred to the fusion chamber (see below) in 200 µl of 0.3 M mannitol, 0.1 mM $MgSO_4$, 0.001 mM $CaCl_2$ in distilled water. Fusion and activation were induced by application of an AC. pulse of 3V for 5 seconds followed by 3 DC. pulses of 1.25 kV/Cm for 80 µsecs. Couplets were then washed in TC199 10% FCS and incubated at 37° C. 5% $CO_2$ for a further period of time sufficient for the formation of a pronucleus prior to being used as nuclear donors for the second stage nuclear transfer embryo reconstruction. Alternatively, the donor nucleus may be transferred by either manual or piezzo aided injection or by any other chemical or physical means of producing cell fusion.

Fusion and Activation

For activation, oocytes were placed between two parallel electrodes in 200 µl of 0.3 M mannitol, 0.1 mM $MgSO_4$, 0.001 mM $CaCl_2$ in distilled water (Willadsen, 1986). Activation was induced by application of 1 DC pulse of 1.25 kV/cm for 80 µs. For fusion manipulated embryos were treated in a similar manner with the addition that the contact surface between the enucleated oocyte and the cell was arranged parallel to the electrodes. Fusion was induced by application of an AC. current of 3V for 5 seconds followed by 3 DC pulses of 1.25 kV/cm for 80 µs Embryo Culture and Assessment (all Groups)

After nuclear transfer reconstructed embryos may be cultured by any method known to the art these include but are not limited to 1. Embryos were double embedded in 1% and 1.2% agar (DIFCO) in PBS and transferred to the ligated oviduct of synchronised or unsynchronised ewes. After 6 days recipient ewes were sacrificed and the embryos retrieved by flushing from the oviduct using PBS 10% FCS. Embryos were dissected from the agar chips using 2 needles and development assessed by microscopy.
2. Alternatively the reconstructed embryos may be transferred directly to the oviduct of a suitable synchronised final recipient host for development to term.
3. Alternatively embryos may be cultured in vitro by any suitable means to a stage suitable for transfer to a synchronized recipient.

The invention claimed is:

1. A method of reconstituting a non-primate mammalian embryo, comprising
   (i) transferring a non-primate mammalian donor nucleus from a diploid somatic cell into a first recipient oocyte;
   (ii) removing the donor nucleus from the first recipient oocyte;
   (iii) providing a second recipient oocyte or enucleated fertilized zygote; and
   (iv) transferring the donor nucleus from the first recipient oocyte into the second recipient oocyte or the enucleated fertilized zygote to obtain a reconstituted non-primate mammalian embryo, wherein the second recipient oocyte is activated prior to, concomitant with or following transfer of the donor nucleus.

2. The method as claimed in claim 1, wherein the first oocyte is a mature metaphase II oocyte or an activated metaphase II oocyte.

3. The method as claimed in claim 1, wherein the second oocyte is an enucleated metaphase II oocyte.

4. The method as claimed in claim 1, in which a reconstructed embryo obtained thereby is cultured in vitro or in vivo to a stage suitable for transfer to a final surrogate recipient for development to term.

5. The method as claimed in claim 1, in which a reconstructed embryo obtained thereby is transferred to a final surrogate recipient to support embryo development and development to term.

6. The method as claimed in claim 1, in which the donor nucleus is genetically modified.

7. The method as claimed in claim 1, wherein the donor nucleus is from a G1 cell.

8. The method as claimed in claim 1, wherein the diploid cell is arrested at the G1/S-phase border.

9. The method as claimed in claim 1, wherein the donor nucleus is donated by a diploid cell arrested by any point in the cell cycle.

10. The method as claimed in claim 1, wherein the first recipient oocyte is enucleated prior to transfer of the donor nucleus into said first recipient oocyte.

11. The method as claimed in claim 1, wherein the donor nucleus is transferred into the first recipient oocyte by cell fusion, or by cell or nuclear injection.

12. The method as claimed in claim 1, in which the non-primate mammalian embryo is an ungulate species embryo.

13. The method as claimed in claim 12, wherein the non-primate mammalian embryo is a cow or bull, pig, sheep, goat, camel, or water buffalo embryo.

14. The method as claimed in claim 1, wherein the non-primate mammalian embryo is a mouse, rat, or other rodent embryo.

15. The method as claimed in claim 1, wherein the non-primate mammalian embryo is a lagomorph embryo.

16. The method as claimed in claim 15, wherein the non-primate lagomorph embryo is a rabbit embryo.

17. The method as claimed in claim 1, wherein the donor nucleus is transferred from the first recipient oocyte to a fertilized zygote.

18. The method as claimed in claim 1, wherein the second recipient oocyte is activated by chemical or physical means.

19. The method as claimed in claim 1, wherein the second recipient oocyte is enucleated.

20. A method of preparing a non-primate mammal, the method comprising:
   (a) transferring a non-primate mammalian donor nucleus from a diploid somatic cell into a first recipient oocyte;
   (b) removing the donor nucleus from the first recipient oocyte;
   (c) either enucleating a second recipient oocyte or enucleating a fertilized zygote of the donor species; and
   (d) transferring the donor nucleus from the first recipient oocyte into the second recipient oocyte or zygote of the same species as the donor to obtain a reconstituted non-primate mammalian embryo, wherein the second recipient oocyte is activated prior to, concomitant with or following transfer of the donor nucleus;
   (e) causing a fetus to develop from the embryo, thereby obtaining a non-primate mammalian fetus; and
   (f) causing a non-primate mammal to develop to term from the non-primate mammalian fetus, thereby obtaining a non-primate mammal.

21. The method as claimed in claim 20, further comprising:
   (g) breeding the non-primate mammal.

22. A method as claimed in claim 20, wherein the non-primate mammalian embryo is further manipulated prior to full development of the embryo.

23. A method as claimed in claim 20, wherein the non-primate mammalian fetus is further manipulated prior to full development of the fetus.

24. The method as claimed in claim 1, further comprising isolating a cell line or cell population from the reconstituted embryo.

25. The method as claimed in claim 20, further comprising isolating a cell line or cell population from the fetus.

26. The method as claimed in claim 20, wherein a new cell line or cell population is derived from the non-primate mammal.

27. The method as claimed in claim 20, wherein more than one non-primate mammal is derived from the reconstituted embryo.

28. The method as claimed in claim 18, wherein the chemical or physical activation is by a treatment that induces calcium entry into the oocyte or release of internal calcium stores.

29. The method as claimed in claim 18, wherein the chemical activation is by treatment with ethanol, ionomycin, inositol tris-phosphate or calcium ionophore A23187.

30. The method as claimed in claim 18, wherein the chemical activation is by treatment with extracts of sperm.

31. The method as claimed in claim 18, wherein the physical activation is by application of a DC electrical stimulus.

32. The method as claimed in any one of claims 28-31, wherein the chemical or physical activation further comprises treatment with inhibitors of protein synthesis or inhibitors of serine threonine protein kinases.

33. The method as claimed in claim 1, wherein the non-primate mammalian embryo is a pig embryo.

34. The method as claimed in claim 12, wherein the non-primate mammalian embryo is a cow embryo.

35. The method as claimed in claim 12, wherein the non-primate mammalian embryo is a sheep embryo.

* * * * *